United States Patent
Kang et al.

(10) Patent No.: US 11,380,853 B2
(45) Date of Patent: Jul. 5, 2022

(54) ORGANIC LIGHT EMITTING DIODE AND ORGANIC LIGHT EMITTING DEVICE INCLUDING THE SAME

(71) Applicants: LG Display Co., Ltd., Seoul (KR); Heesung Material Co., Ltd., Yongin-si (KR)

(72) Inventors: Hye-Seung Kang, Paju-si (KR); Do-Han Kim, Paju-si (KR); Woo-Sam Kim, Paju-si (KR); Dong-Jun Kim, Paju-si (KR); Hyo-Kyun Ham, Paju-si (KR); Young-Seok No, Paju-si (KR)

(73) Assignees: LG DISPLAY CO., LTD., Seoul (KR); HEESUNG MATERIAL CO., LTD., Yongin-si (KR)

( * ) Notice: Subject to any disclaimer, the term of this patent is extended or adjusted under 35 U.S.C. 154(b) by 351 days.

(21) Appl. No.: 16/725,917

(22) Filed: Dec. 23, 2019

(65) Prior Publication Data
US 2020/0212312 A1    Jul. 2, 2020

(30) Foreign Application Priority Data
Dec. 28, 2018    (KR) .................. 10-2018-0172141

(51) Int. Cl.
*H01L 51/50*    (2006.01)
*H01L 51/00*    (2006.01)
(Continued)

(52) U.S. Cl.
CPC ........ *H01L 51/0072* (2013.01); *C07C 211/61* (2013.01); *C07D 409/14* (2013.01);
(Continued)

(58) Field of Classification Search
None
See application file for complete search history.

(56) References Cited

U.S. PATENT DOCUMENTS 6,660,410 B2    12/2003    Hosokawa
7,651,786 B2    1/2010    Matsuura et al.
(Continued)

FOREIGN PATENT DOCUMENTS

| EP | 3336159 A1 | 6/2018 |
|---|---|---|
| KR | 10-2018-0060696 A | 6/2018 |
| KR | 10-2018-0096444 A | 8/2018 |

*Primary Examiner* — Gregory D Clark
(74) *Attorney, Agent, or Firm* — Birch, Stewart, Kolasch & Birch, LLP

(57) ABSTRACT

Disclosed is an organic light emitting diode including a first electrode; a second electrode facing the first electrode; and a first emitting material layer, which includes a first host, a second host and a first dopant and disposed between the first and second electrodes. The first host is represented by Formula 1, the second host may be a triazine derivative, and the first dopant may be a red, green or blue dopant.

25 Claims, 6 Drawing Sheets

[Formula 1]

(51) Int. Cl.
*C07C 211/61* (2006.01)
*C07D 409/14* (2006.01)
*C07D 487/04* (2006.01)
*C09K 11/06* (2006.01)
*H01L 27/32* (2006.01)
*H01L 51/52* (2006.01)

(52) U.S. Cl.
CPC ............ *C07D 487/04* (2013.01); *C09K 11/06* (2013.01); *H01L 51/006* (2013.01); *H01L 51/0067* (2013.01); *H01L 51/0074* (2013.01); *C07C 2603/18* (2017.05); *C07C 2603/97* (2017.05); *C09K 2211/1018* (2013.01); *H01L 27/322* (2013.01); *H01L 27/3211* (2013.01); *H01L 51/0056* (2013.01); *H01L 51/0058* (2013.01); *H01L 51/504* (2013.01); *H01L 51/5016* (2013.01); *H01L 51/5056* (2013.01); *H01L 51/5278* (2013.01); *H01L 2251/5384* (2013.01)

(56) References Cited

U.S. PATENT DOCUMENTS

| | | |
|---|---|---|
| 2010/0078631 A1 | 4/2010 | Pieh |
| 2017/0213988 A1* | 7/2017 | Park et al. ............... H01l 51/50 428/690 |

* cited by examiner

100

D

ORGANIC LIGHT EMITTING DIODE AND ORGANIC LIGHT EMITTING DEVICE INCLUDING THE SAME

CROSS-REFERENCE TO RELATED APPLICATIONS

The present application claims priority to Korean Patent Application No. 10-2018-0172141 filed in Republic of Korea on Dec. 28, 2018, which is hereby incorporated by reference in its entirety into the present application.

BACKGROUND

Field of Technology

The present disclosure relates to an organic light emitting diode and more particularly to an organic light emitting diode having improved emitting efficiency and lifespan and an organic light emitting device including the organic light emitting diode.

Discussion of the Related Art

Recently, requirements for flat panel display devices having small occupied area has increased. Among the flat panel display devices, a technology of an organic light emitting display device including an organic light emitting diode (OLED) is rapidly developing.

The OLED emits light by injecting electrons from a cathode as an electron injection electrode and holes from an anode as a hole injection electrode into an emitting material layer (EML), combining the electrons with the holes, generating an exciton, and transforming the exciton from an excited state to a ground state. A flexible substrate, for example, a plastic substrate, can be used as a base substrate where elements are formed. In addition, the organic light emitting display device can be operated at a voltage (e.g., 10V or below) lower than a voltage required to operate other display devices. Moreover, the organic light emitting display device has advantages in the power consumption and the color sense.

In the fluorescent material, only singlet exciton is involved in the light emission such that the fluorescent material has low emitting efficiency. On the other hand, in the phosphorescent material, the triplet exciton as well as the singlet exciton is involved in the light emission such that the phosphorescent has higher emitting efficiency that the fluorescent material.

However, there is still a limitation in the emitting efficiency and the lifespan even though the phosphorescent material is used.

SUMMARY

Accordingly, the present disclosure is directed to an organic light emitting diode (OLED) and an organic light emitting device including the same that substantially obviate one or more of the problems due to limitations and disadvantages of the related art.

Additional features and advantages of the present disclosure are set forth in the description which follows, and will be apparent from the description, or evident by practice of the present disclosure. The objectives and other advantages of the present disclosure are realized and attained by the features described herein as well as in the appended drawings.

To achieve these and other advantages and in accordance with the purpose of the present disclosure, as embodied and broadly described herein, an organic light emitting diode comprises a first electrode; a second electrode facing the first electrode; and a first emitting material layer including a first host, a second host and a first dopant and disposed between the first and second electrodes, wherein the first host is represented by Formula 1: wherein X is O or S, wherein $Ar_1$ is C10 to C30 aryl, and $Ar_2$ is C6 to C30 aryl, wherein each of $R_1$ to $R_3$ is independently selected from the group consisting of halogen, C1 to C10 alkyl, C1 to C20 aryl and C3 to C10 cycloalkyl, and wherein each of a, b and c is independently an integer of 0 to 4.

[Formula 1]

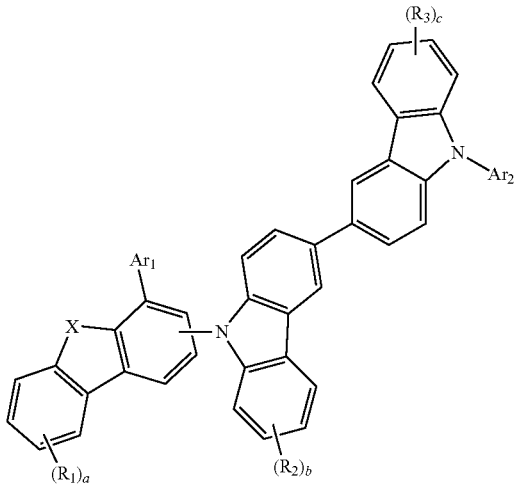

In another aspect, an organic light emitting device comprises a substrate; and an organic light emitting diode on or over the substrate, the organic light emitting diode comprising: a first electrode; a second electrode facing the first electrode; and a first emitting material layer including a first host, a second host and a first dopant and disposed between the first and second electrodes, wherein the first host is represented by Formula 1: wherein X is O or S, wherein $Ar_1$ is C10 to C30 aryl, and $Ar_2$ is C6 to C30 aryl, wherein each of $R_1$ to $R_3$ is independently selected from the group consisting of halogen, C1 to C1.0 alkyl, C1 to C20 aryl and C3 to C10 cycloalkyl, and wherein each of a, b and c is independently an integer of 0 to 4.

[Formula 1]

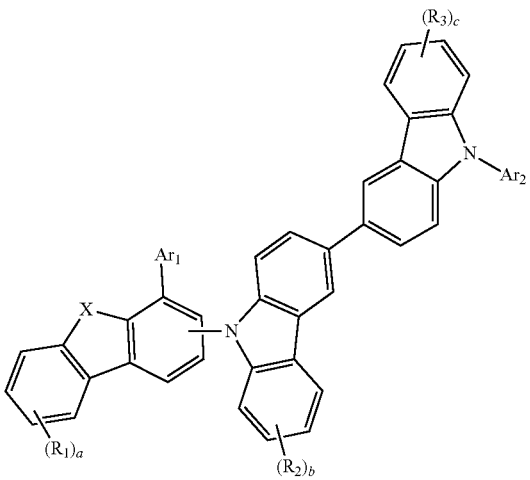

It is to be understood that both the foregoing general description and the following detailed description are exemplary and explanatory and are intended to further explain the present disclosure as claimed.

BRIEF DESCRIPTION OF THE DRAWINGS

The accompanying drawings, which are included to provide a further understanding of the present disclosure and are incorporated in and constitute a part of this specification, illustrate embodiments of the present disclosure and together with the description serve to explain the principles of the present disclosure.

DETAILED DESCRIPTION

Reference will now be made in detail to some of the examples and preferred embodiments, which are illustrated in the accompanying drawings.

Figure 1:
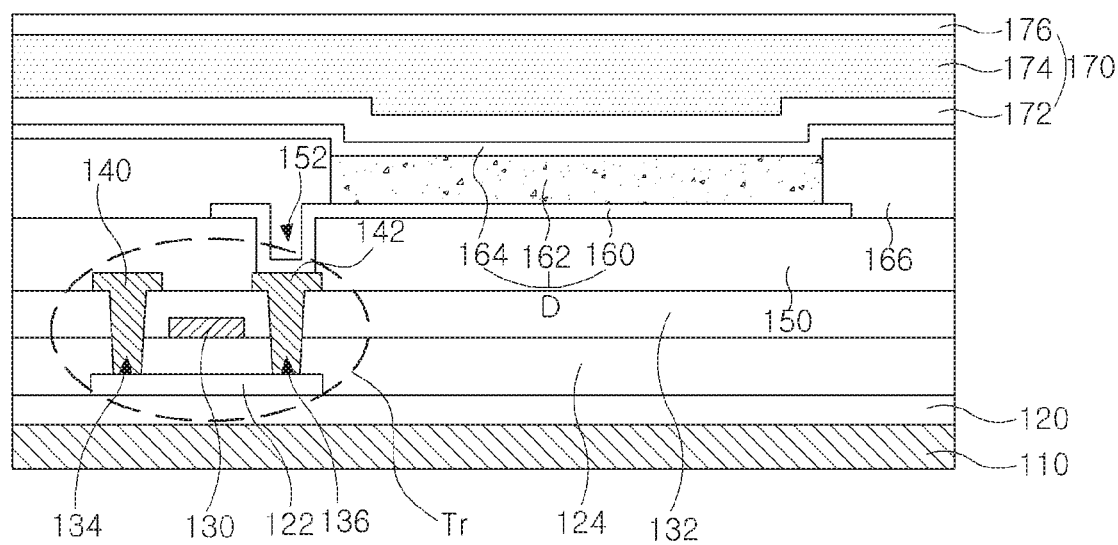
FIG. 1 is a schematic cross-sectional view of an organic light emitting device according to a first embodiment of the present disclosure.

FIG. 1 is a schematic cross-sectional view of an organic light emitting device according to a first embodiment of the present disclosure.

As shown in FIG. 1, the organic light emitting device 100 includes a substrate 110, a TFT Tr and an OLED D connected to the TFT Tr. For example, a red pixel, a green pixel and a blue pixel are defined in the substrate 110, and the OLED D is positioned in each pixel. Namely, the red light, the green light and the blue light of OLED D are respectively formed in the red pixel, the green pixel and the blue pixel such that the organic light emitting device 100 can provide a full-color image.

The substrate 110 may be a glass substrate or a plastic substrate. For example, the substrate 110 may be a polyimide substrate.

A buffer layer 120 is formed on the substrate, and the TFT Tr is formed on the buffer layer 120. The buffer layer 120 may be omitted.

A semiconductor layer 122 formed on the buffer layer 120. The semiconductor layer 122 may include an oxide semiconductor material or polycrystalline silicon.

When the semiconductor layer 122 includes the oxide semiconductor material, a light-shielding pattern may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 1, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element.

In the TFT Tr, the gate electrode 130, the source electrode 140, and the drain electrode 142 are positioned over the semiconductor layer 122. Namely, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

The gate line and the data line cross each other to define the pixel region, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A passivation layer 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel region. The first electrode 160 may be an anode and may be formed of a conductive material having a relatively high work function. For example, the first electrode 160 may be formed of a transparent conductive material such as indium-tin-oxide (ITO) or indium-zinc-oxide (170).

When the OLED device 100 is operated in a top-emission type, a reflection electrode or a reflection layer may be formed under the first electrode 160. For example, the reflection electrode or the reflection layer may be formed of aluminum-palladium-copper (APC) alloy.

A bank layer 166 is formed on the passivation layer 150 to cover an edge of the first electrode 160. Namely, the bank layer 166 is positioned at a boundary of the pixel region and exposes a center of the first electrode 160 in the pixel region.

An organic emitting layer 162 is formed on the first electrode 160. The organic emitting layer 162 has a single-layered structure of an emitting material layer (EML). Alternatively, to improve an efficiency of the OLED D, the organic emitting layer 162 may have a multi-layered structure. For example, the organic emitting layer 162 may further include a hole injection layer (HIL) and a hole transporting layer (HTL), which are sequentially stacked between the first electrode 160 and the EML, and an electron transporting layer (ETL) and an electron injection layer (EIL), which are sequentially stacked between the EML and the second electrode 164.

In addition, the organic emitting layer 163 may further include an electron blocking layer (EBL) between the HTL and the EML and a hole blocking layer (HBL) between the EML and the ETL.

The organic emitting layer 162 may emit different color light in the red, green and blue pixels. Namely, the organic emitting layer 162 including a host and a red dopant is formed in the red pixel, the organic emitting layer 162 including a host and a green dopant is formed in the green pixel, and the organic emitting layer 162 including a host and a blue dopant is formed in the blue pixel.

A second electrode 164 is formed over the substrate 110 where the organic emitting layer 162 is formed. The second electrode 164 covers an entire surface of the display area and may be formed of a conductive material having a relatively low work function to serve as a cathode. For example, the second electrode 164 may be formed of aluminum (Al), magnesium (Mg) or Al—Mg alloy.

The first electrode 160, the organic emitting layer 162 and the second electrode 164 constitute the OLED D.

An encapsulation film 170 is formed on the second electrode 164 in prevent penetration of moisture into the OLED D. The encapsulation film 170 includes a first inorganic insulating layer 172, an organic insulating layer 174 and a second inorganic insulating layer 176 sequentially stacked, but it is not limited thereto. The encapsulation film 170 may be omitted.

A polarization plate for reducing an ambient light reflection may be disposed over the top-emission type OLED D. For example, the polarization plate may be a circular polarization plate.

In addition, a cover window may be attached to the encapsulation film 170 or the polarization plate. In this instance, the substrate 110 and the cover window have a flexible property such that a flexible display device may be provided.

Figure 2:
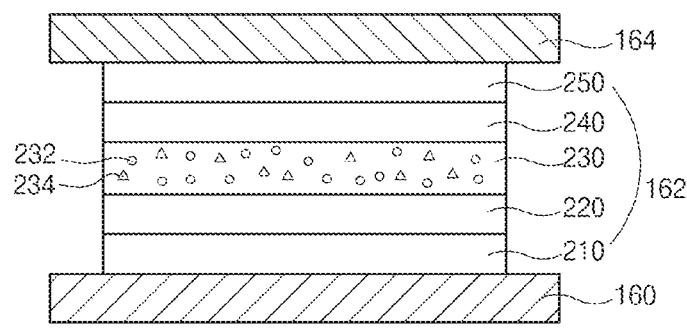
FIG. 2 is a schematic cross-sectional view of an OLED for the organic light emitting device according to the first embodiment of the present disclosure.

FIG. 2 is a schematic cross-sectional view of an OLED for the organic light emitting device according to the first embodiment of the present disclosure.

As shown in FIG. 2, the OLED D includes the first and second substrates 160 and 164, which face each other, and the organic emitting layer 162 therebetween. The organic emitting layer 162 includes an emitting material layer (EML) 230 between the first and second electrodes 160 and 164 and a hole transporting layer (HTL) 220 between the first electrode 160 and the EML 230.

The EML 230 may have a thickness being greater than the HTL 220. For example, the EML 230 may have a thickness of about 5 to 50 nm, and the HTL may have a thickness of about 1 to 40 nm.

In addition, the organic emitting layer 162 may further include an electron transporting layer (ETL) 240 between the second electrode 164 and the EML 230.

Moreover, the organic emitting layer 162 may further include a hole injection layer (HIL) 210 between the first electrode 160 and the HTL 220 and an electron injection layer (EIL) 250 between the second electrode 164 and the ETL 240.

Although not shown, the organic emitting layer 162 may further include an electron blocking layer (EBL) between the HTL 220 and the EML 230 and a hole blocking layer (HBL) between the EML 230 and the ETL 240.

At least one of the HIL 210, the EBL, the HBL, the ETL 240 and the EIL 250 may be omitted.

The EML 230 includes a first host 232 having a p-type property, i.e., a hole type property, a second host 234 having an n-type property, i.e., an electron type property, and a dopant. For example, a percentage by weight of the first host 232 may be equal to or greater than that of the second host 234. The dopant may have a percentage by weight of about 5 to 25 in the EML 230.

For example, the first host 232 may be represented by Formula 1.

[Formula 1]

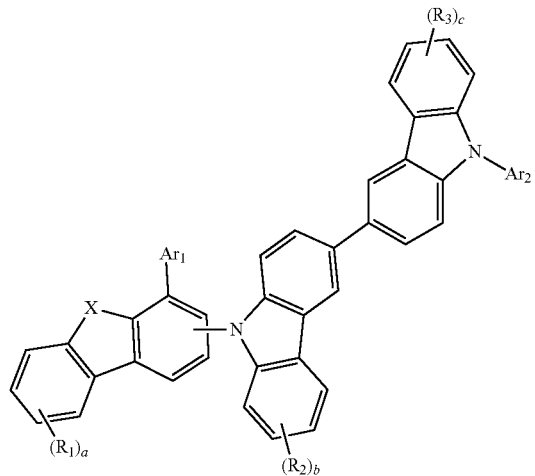

In Formula 1, X is O or S. An is C10 in C30 aryl, and $Ar_2$ is C6 to C30 aryl. Each of $R_1$ to $R_3$ is independently selected from the group consisting of halogen, C1 to C10 alkyl, C1 to C20 aryl and C3 to C10 cycloalkyl. In addition, each of a, b and c is independently an integer of 0 to 4. The number of carbon atom of $Ar_1$ may be equal to or greater than that of $Ar_2$.

For example, $Ar_1$ may be selected from biphenyl, terphenyl, indenyl, naphthyl, phenanthrenyl, triphenylenyl, fluoranthenyl and fluorenyl, and $Ar_2$ may be selected from phenyl and biphenyl.

The first host 232 is a compound including a biscarbazole moiety and one of a dibenzofuran moiety and a dibenzothiophene moiety, in which an aryl group is bonded (connected) to a first position of the one of the dibenzofuran moiety and the dibenzothiophene moiety. As a result, the first host 232 has high energy level of a triplet state. The energy level of the triplet state of the first host 232 may be in a range of about 2.6 to 2.8 eV.
For example, the first host 232 may be selected from Formula 2.
[Formula 2]
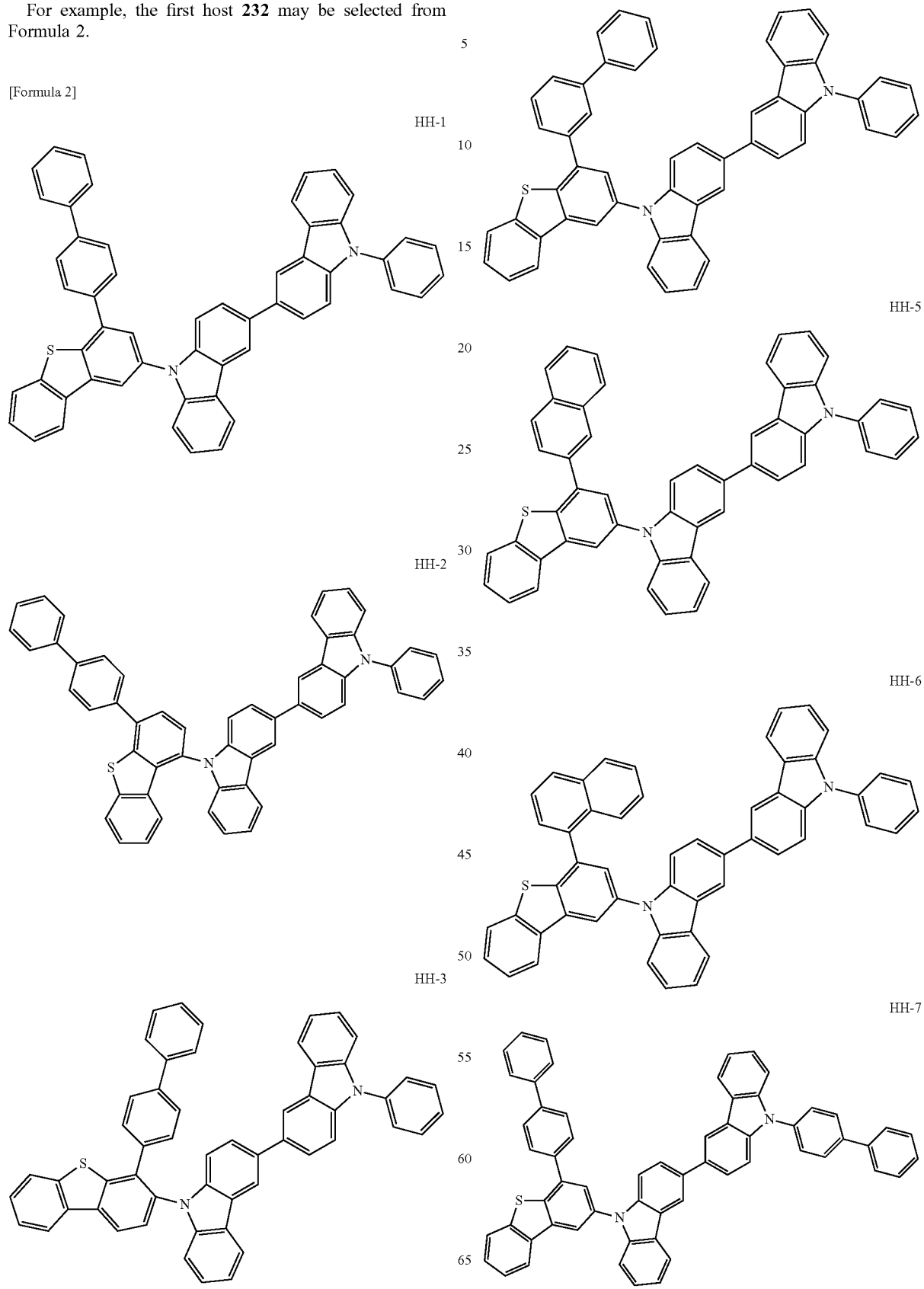

HH-8
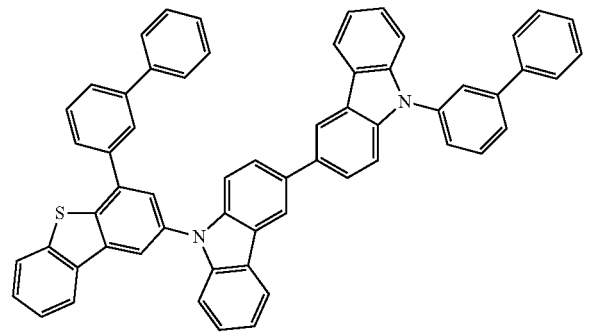
HH-12
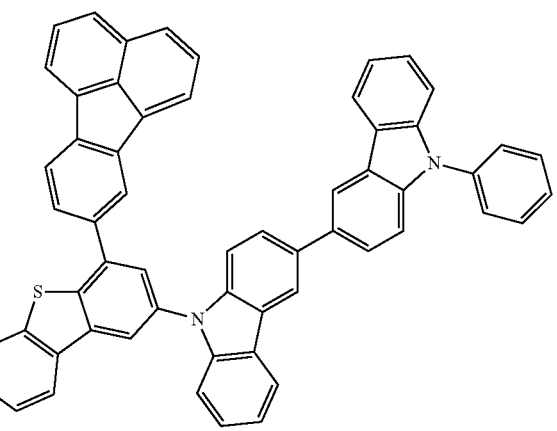
HH-9
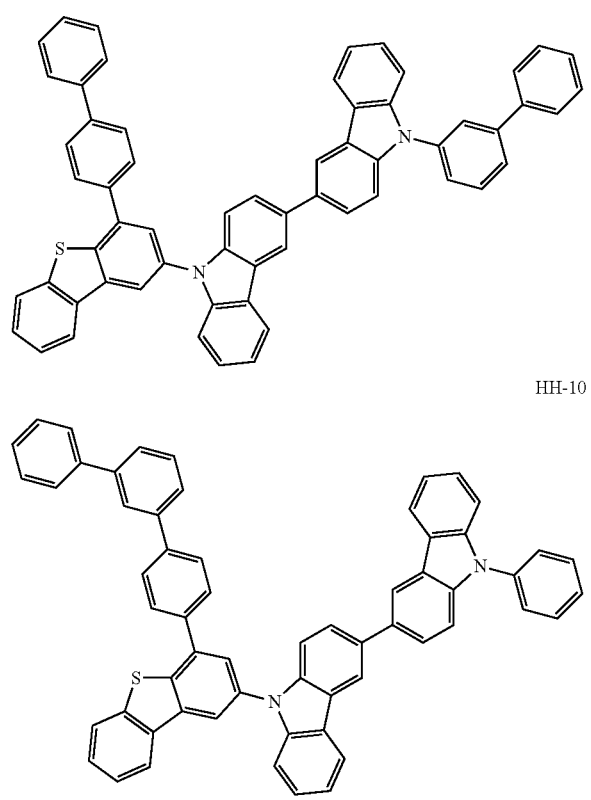
HH-13
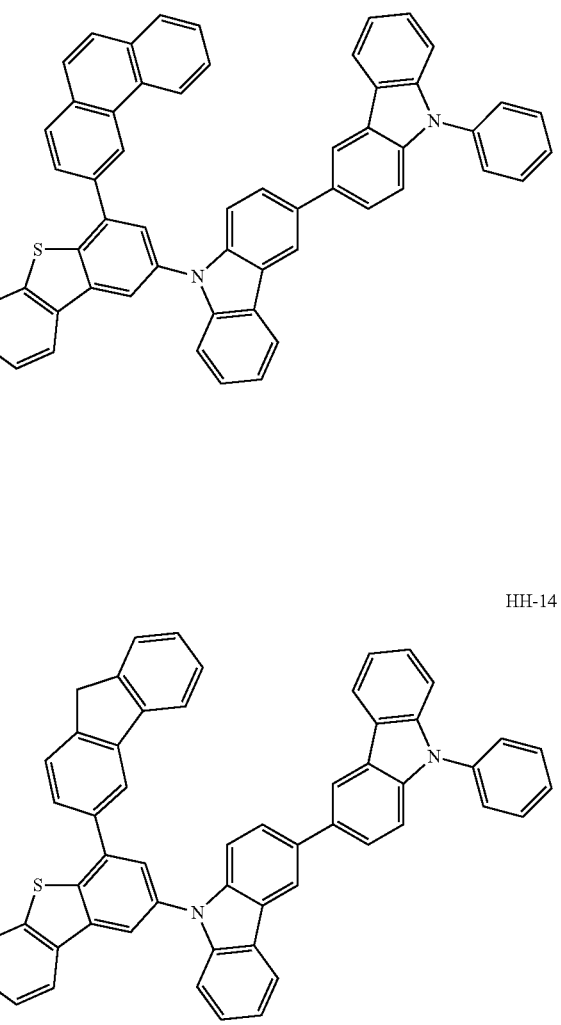
HH-10
HH-11
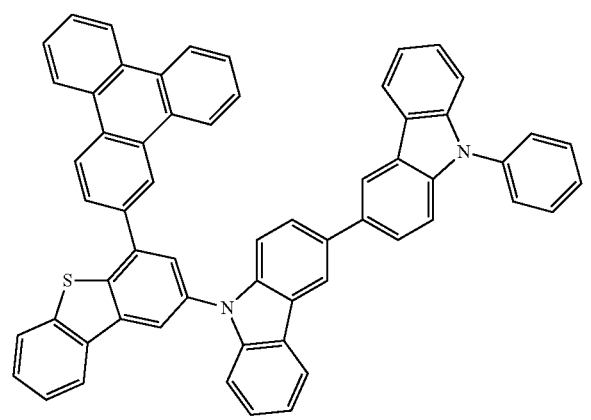
HH-14

HH-15
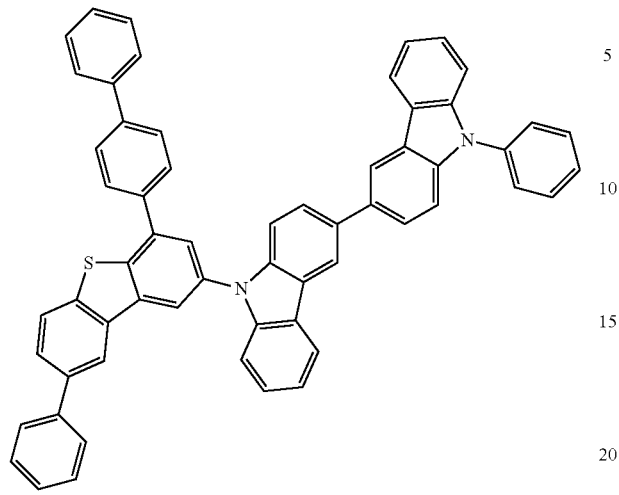
HH-18
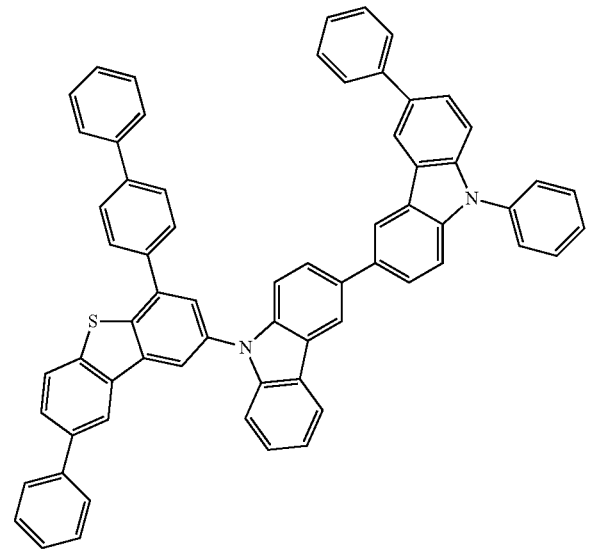
HH-16
HH-19
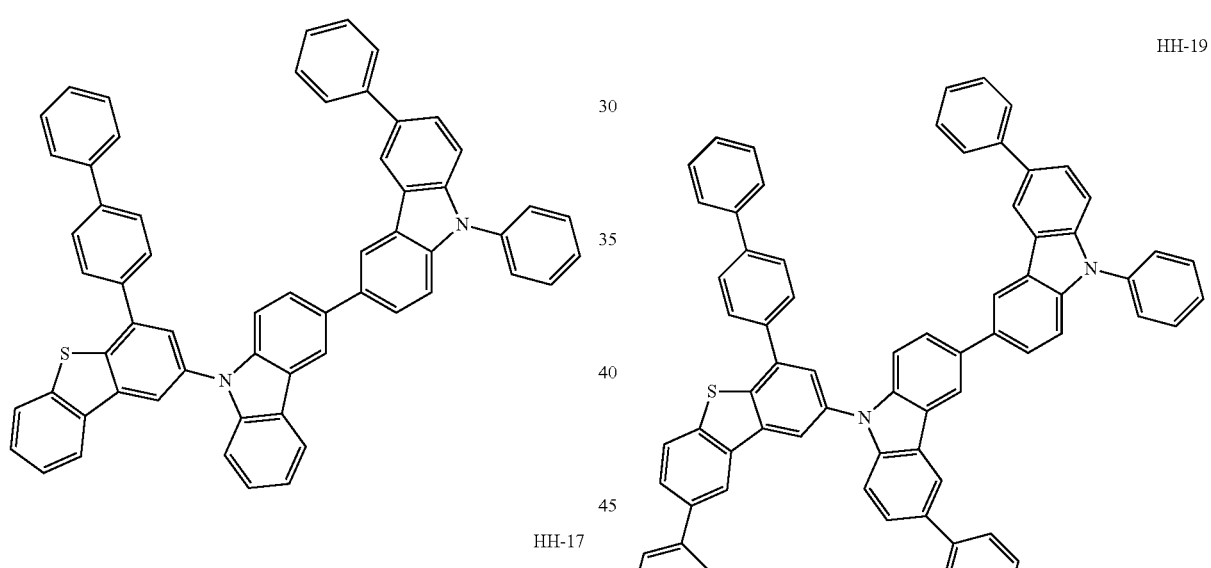
HH-17
HH-20
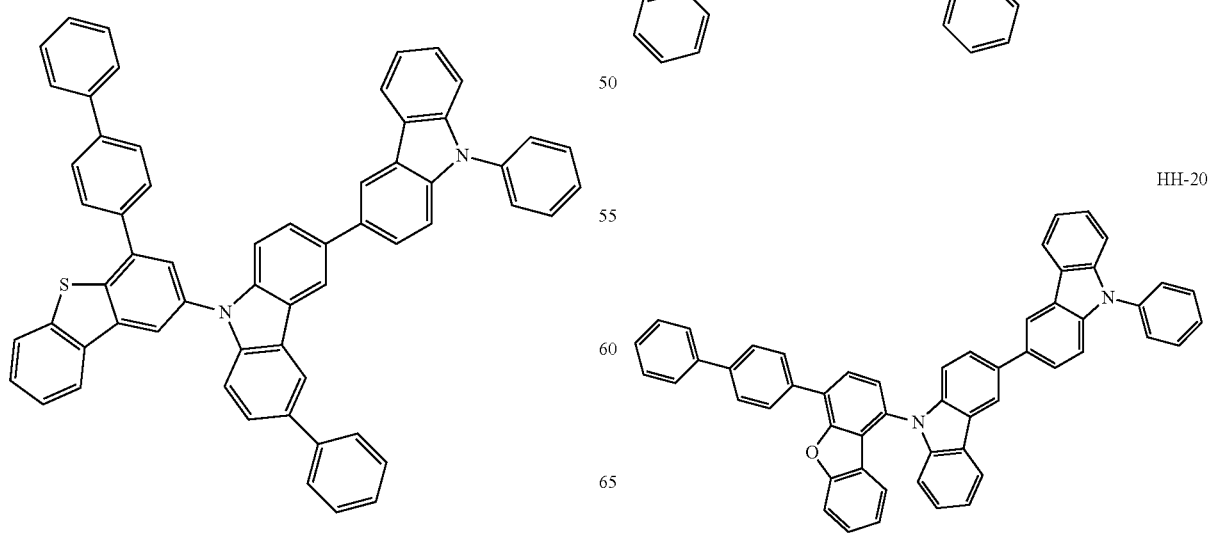

HH-21
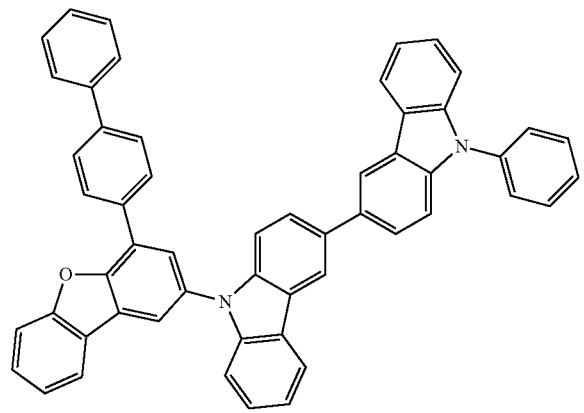
HH-24
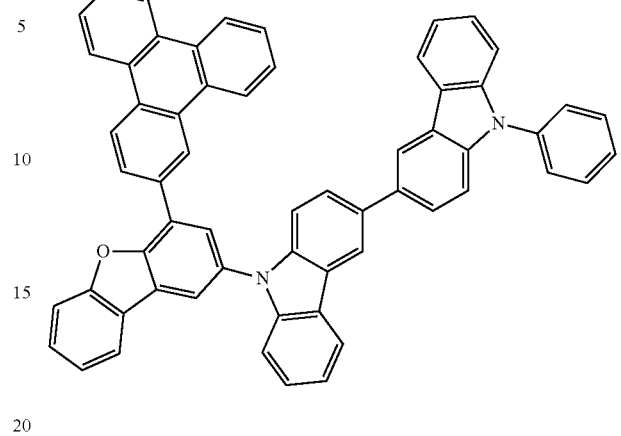
HH-22
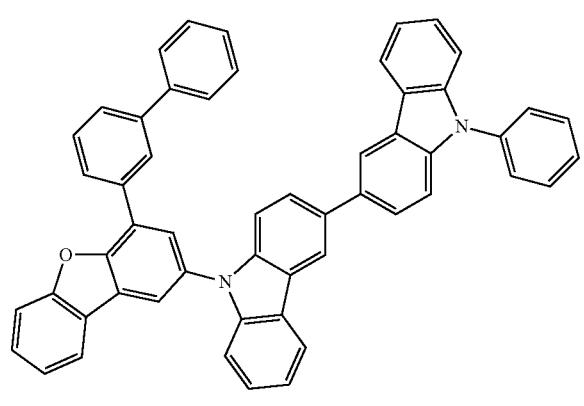
HH-25
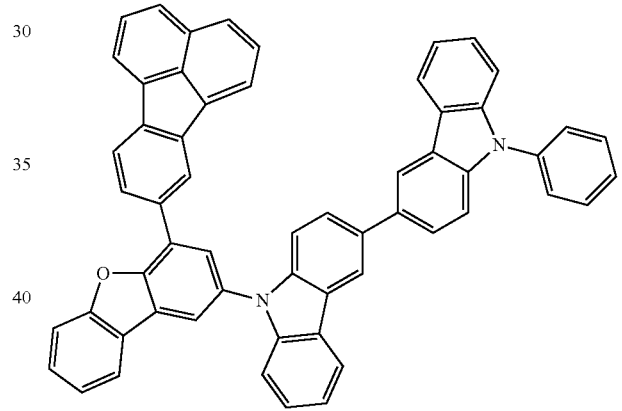
HH-23
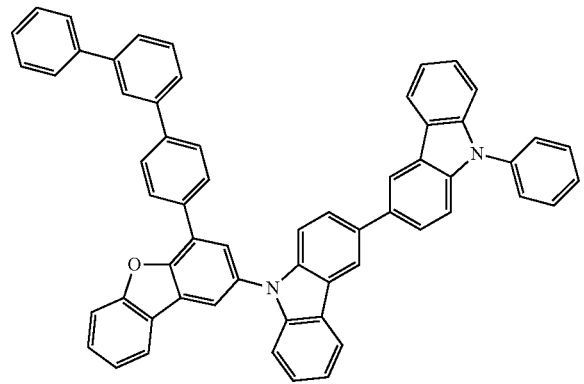
HH-26
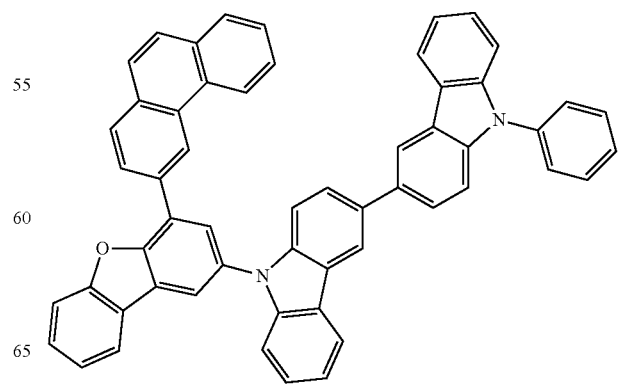

HH-27
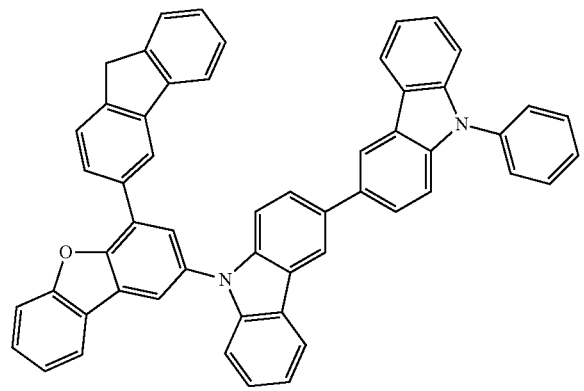
HH-28
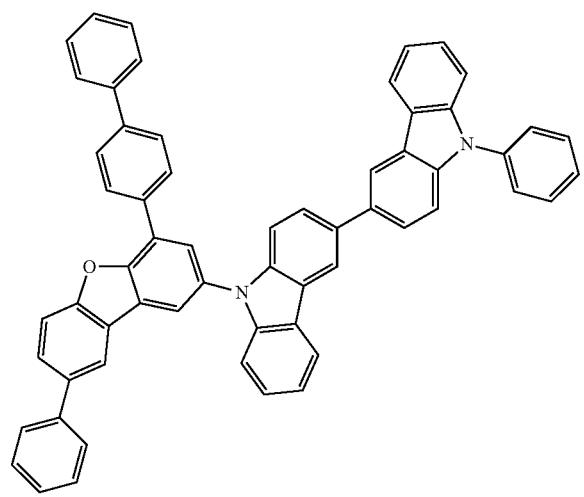
HH-29
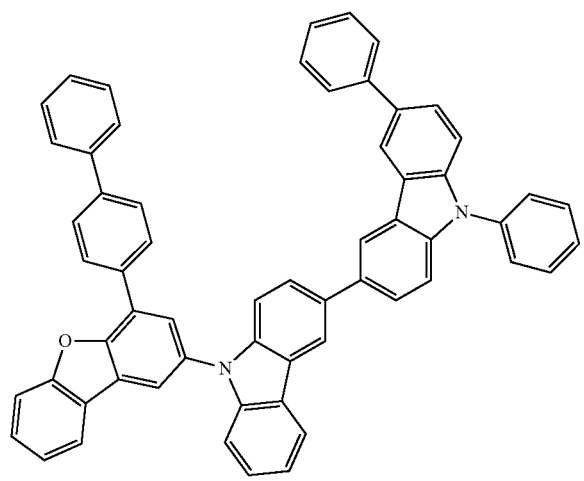
HH-30
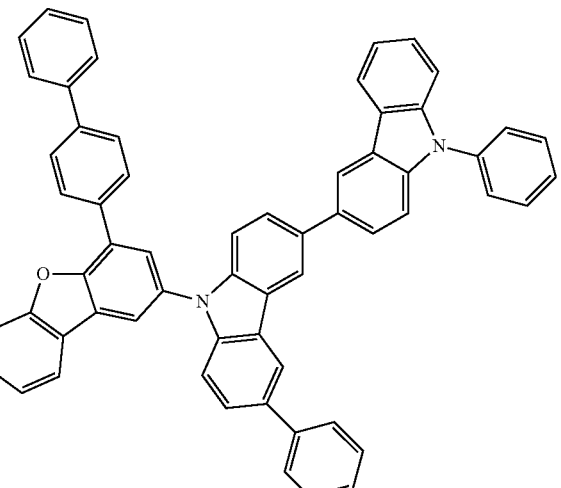
HH-31
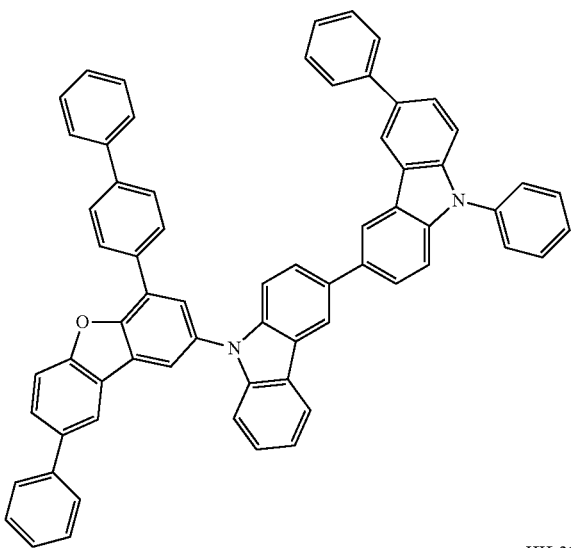
HH-32
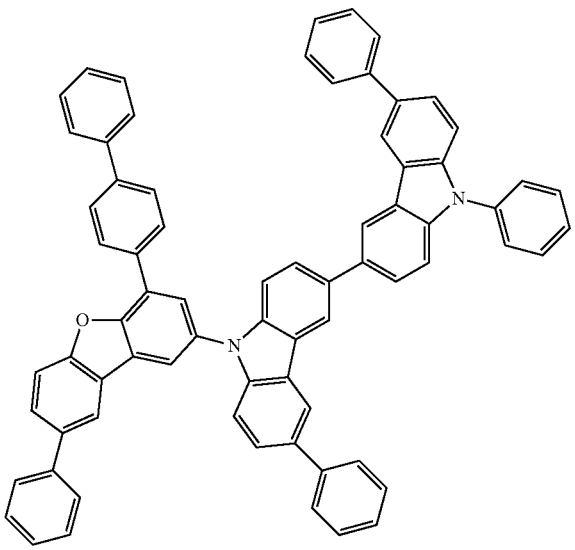

[Synthesis of Compound HH-1]
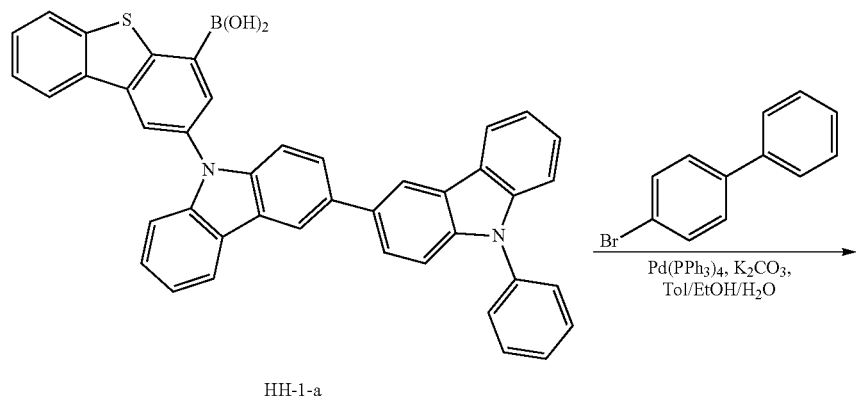
HH-1-a
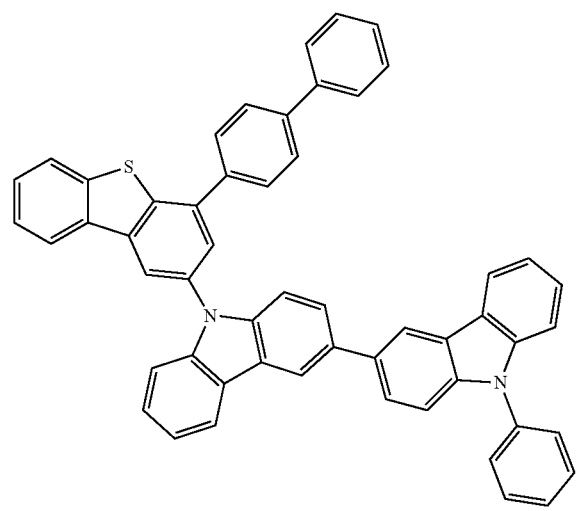
HH-1

The compound HH-1-a (6.7 g, 10.5 mM), 4-bromobiphenyl (2.8 g, 12.0 mM), Pd(PPh$_3$)$_4$(0.6 g, 0.52 mM) and K$_2$CO$_3$(2.9 g, 21.0 mM) were dissolved in a solution of toluene/EtOH/H$_2$O (100/20/20 mL), and the mixture was refluxed for 12 hrs. After completion of reaction, the mixture was extracted using the distilled water and dichloromethane (DCM) under the room temperature, and the organic layer was dried by MgSO$_4$. The solvent was removed by using the rotary evaporator. The resultant was purified by column chromatography using DCM and hexane (volume ratio-1:3) and was recrystallized by methanol such that the compound was obtained.

The second host 234 is a triazine derivative and is represented by Formula 3-1.

[Formula 3-1]

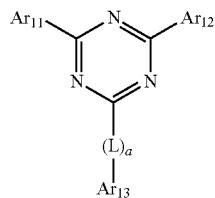

In Formula 3-1, each of Ar$_{11}$ and Ar$_{12}$ is independently selected from the group consisting of hydrogen and C6 to C30 aryl, L is C6 to C30 arylene group, and a is 0 or 1.

In addition, Ar$_{13}$ is a substituted heteroaryl or a fused heteroaryl. Ar$_{13}$ may be represented by Formula 3-2 or Formula 3-3.

[Formula 3-2]

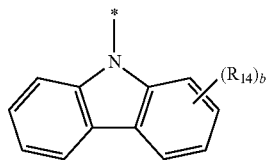

[Formula 3-3]

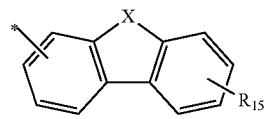

In Formula 3-2, R$_{14}$ is a heteroaryl, or adjacent two R$_{14}$ form a fused ring. In addition, b is an integer of 0 to 4. In Formula 3-3, R$_{15}$ is a heteroaryl, and X is O or S.

The second host 234 is a compound including a first moiety of triazine and a second moiety of carbazole or dibenzofuran, in which the first and second moieties are connected to each other in direct or through a linker. The second host 234 may has an energy level of a triplet state of about 2.4 to 2.8 eV. The energy level of the triplet state of the second host 234 may be equal to or smaller than that of the first host 232. A difference between energy level of the triplet state of the first host 232 and the energy level of the triplet state of the second host 234 may be equal to or less than 0.4 eV.

For example, the second host 234 may be selected from Formula 4.

[Formula 4]

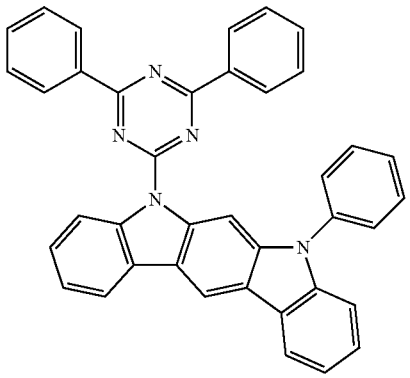

EH-1

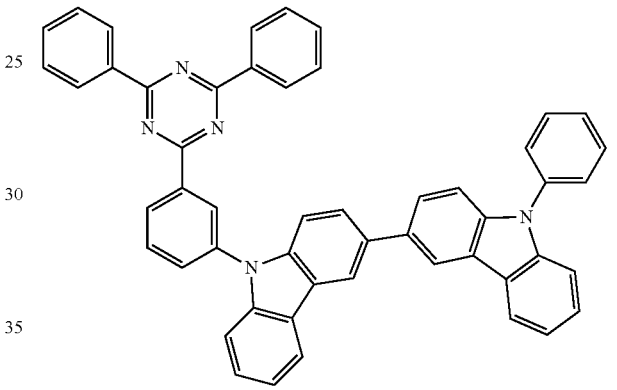

EH-2

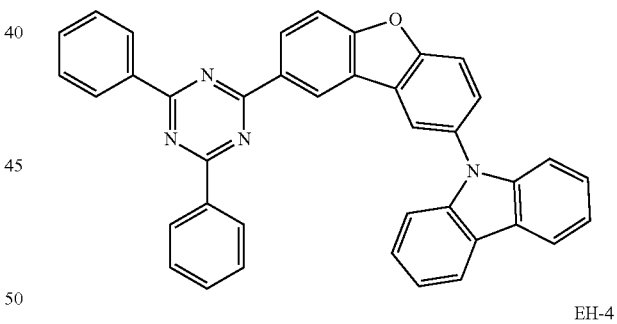

EH-3

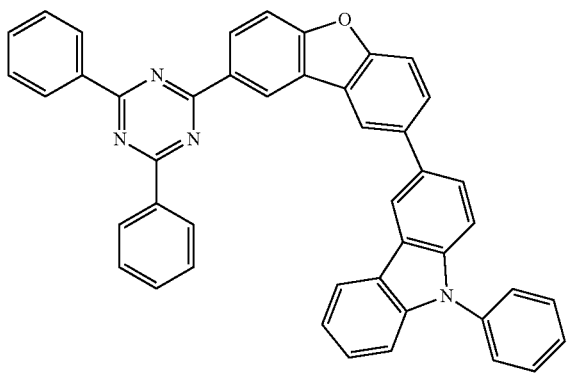

EH-4

The EML 230 may be a green EML, and the dopant, i.e., a green dopant, of the EML 230 may be represented by Formula 5-1 or Formula 5-2. But it is not limited thereto.

[Formula 5-1]

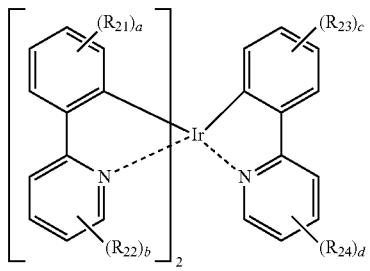

[Formula 5-2]

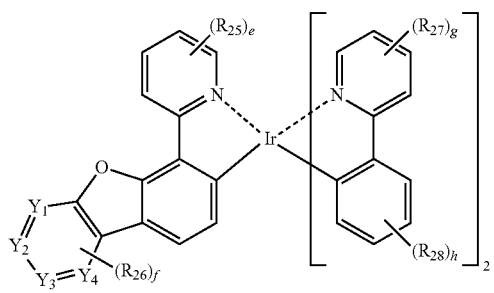

In Formulas 5-1 and 5-2, each of $R_{21}$ to $R_{28}$ is independently selected from the group consisting of deuterium, halogen, C1 to C10 alkyl, C3 to C10 cycloalkyl, C6 to C30 aryl and C5 to C30 heteroaryl. Each of $Y_1$ to $Y_4$ is independently nitrogen (N) or $CR_{29}$. At least one of $Y_1$ to $Y_4$ is N, and at least one of $Y_1$ to $Y_4$ is $CR_{29}$, $CR_{29}$ is selected from the group consisting of deuterium, halogen, C1 to C10 alkyl, C3 to C10 cycloalkyl, C6 to C30 aryl and C5 to C30 heteroaryl. In addition, each of a, c, d, e, g and h is independently an integer of 0 to 4, and each of b and f is independently an integer of 0 to 3.

An energy level of a triplet state of the green dopant is equal to or lower than that of each of the first and second hosts 232 and 234.

For example, the green dopant may be one of [bis(2-phenylpyridine)](pyridyl-2-benzofuro[2,3-b]pyridine) iridium, fac-tris(2-phenylpyridine)iridium(III), bis(2-phenylpyridine)(acetylacetonate)iridium(III), tris[2-(p-tolyl)pyridine]iridium(III), bis(2-(naphthalene-2-yl)pyridine) (acetylacetonate)iridium(III), tris(2-phenyl-3-methylpyridine)iridium, and fac-tris(2-(3-p-xylyl)phenyl)pyridine iridium(III).

In the OLED D of the present disclosure, the EML 230 includes the first host 232, which is a compound including a biscarbazole moiety and one of a dibenzofuran moiety and a dibenzothiophene moiety, in which an aryl group is bonded (connected) to a first position of the one of the dibenzofuran moiety and the dibenzothiophene moiety, and the second host 234, which is a compound including a first moiety of triazine and a second moiety of carbazole or dibenzofuran, in which the first and second moieties are connected to each other in direct or through a linker, such that the emitting efficiency and the lifespan of the OLED D is improved.

The EML is a green EML including the green dopant. Alternatively, the EML may be a red EML including the first host 232, the second host 234 and a red dopant.

The HTL 220 includes a hole transporting material. An energy level of a triplet state of the hole transporting material is substantially equal to that of the first host 232 and is higher than that of the second host 234. As a result, the emitting efficiency and the lifespan of the OLED D are further improved. The energy level of the triplet state of the hole transporting material may be in a range of about 2.4 to 3.0 eV.

The hole transporting material may be represented by Formula 6. Namely, the hole transporting material is an aromatic amine compound substituted by spiro-fluorene group.

[Formula 6]

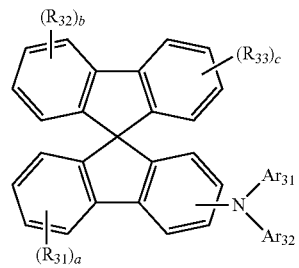

In Formula 6, each of $R_{31}$ to $R_{33}$ is independently selected from the group consisting of deuterium, halogen, C1 to C10 alkyl, C3 to C10 cycloalkyl, C6 to C30 aryl, C5 to C30 heteroaryl, trialkylsilyl and triarylsilyl. Each of $Ar_{31}$ and $Ar_{32}$ is independently selected from the group consisting of C6 to C30 aryl and C5 to C30 heteroaryl. Each of a, b and c is independently an integer of 0 to 4.

For example, each of $Ar_{31}$ and $Ar_{32}$ may be independently selected from the group consisting of phenyl, biphenyl, terphenyl, naphthyl, phenanthryl, fluorenyl, triphenylenyl, dibenzofuranyl and dibenzothiophenyl.

The hole transporting material may be selected from Formula 7.

[Formula 7]

HTL-1

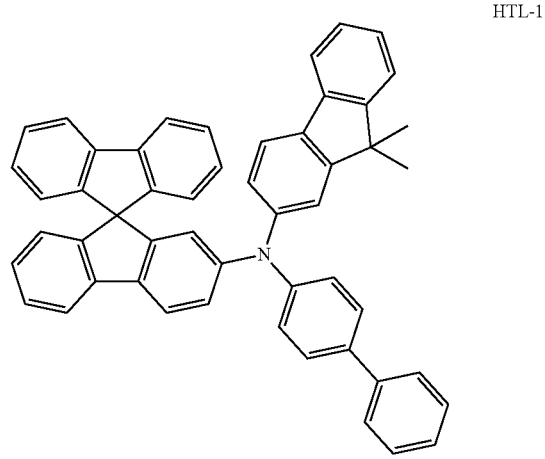

HTL-2
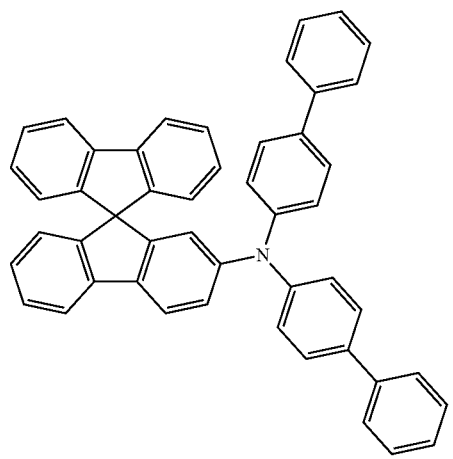
HTL-3
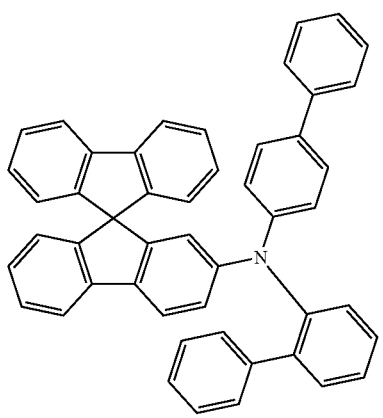
HTL-4
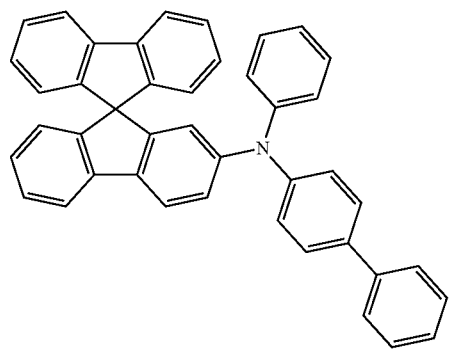
HTL-5
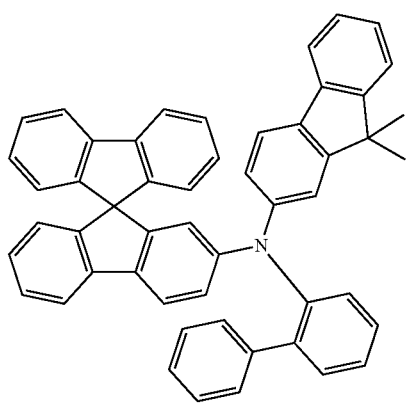
HTL-6
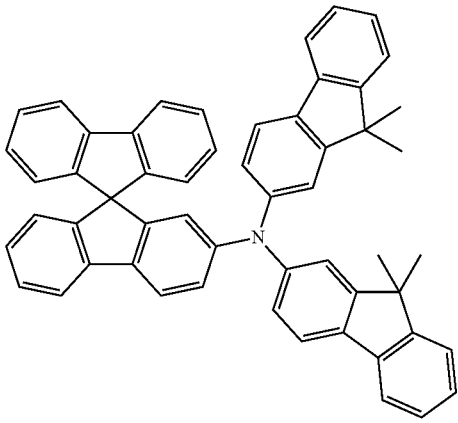
HTL-7
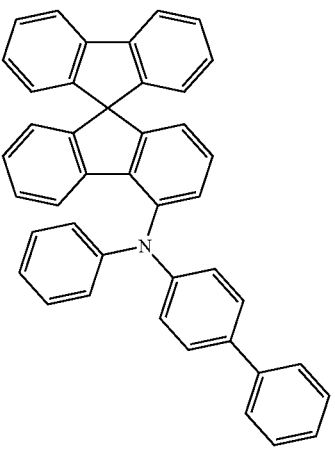
HTL-8
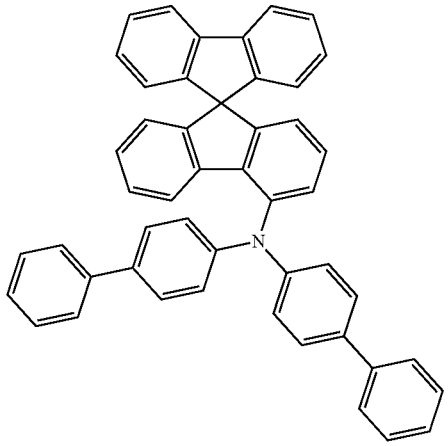

HTL-9
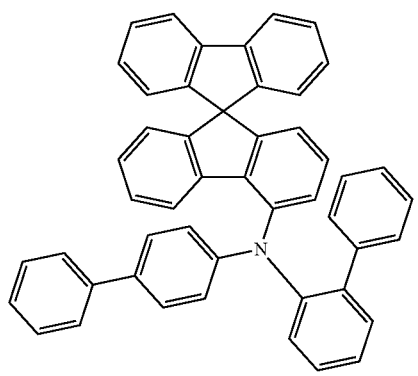
HTL-10
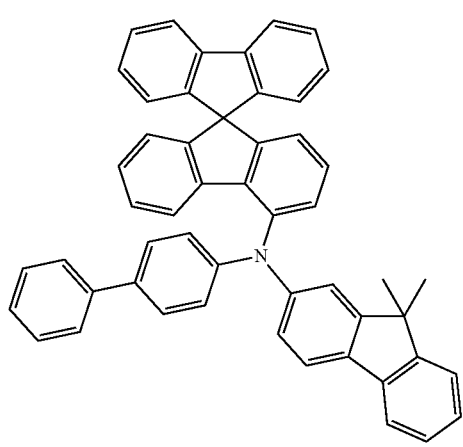
HTL-11
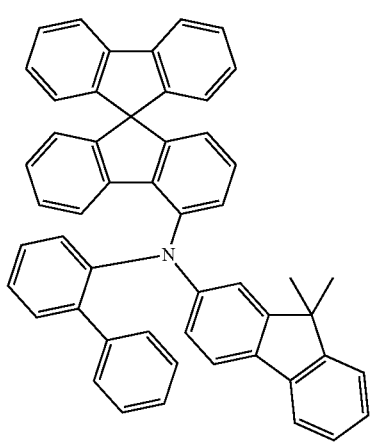
HTL-12
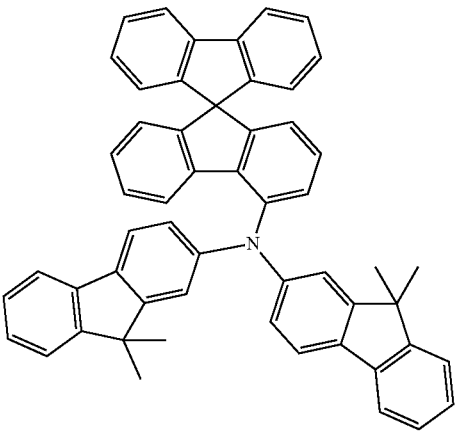
HTL-13
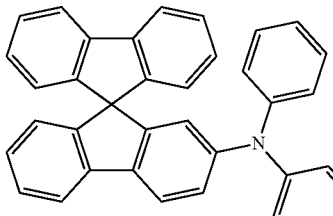
HTL-14
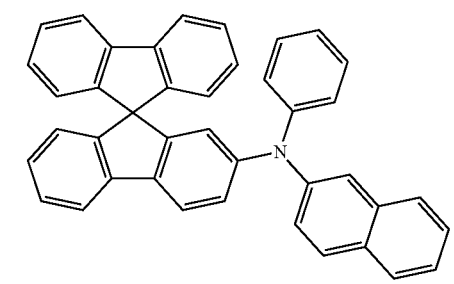
HTL-15
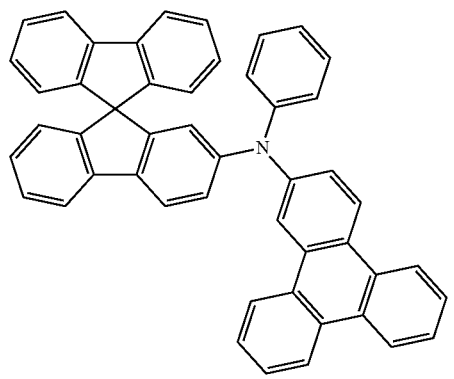

-continued

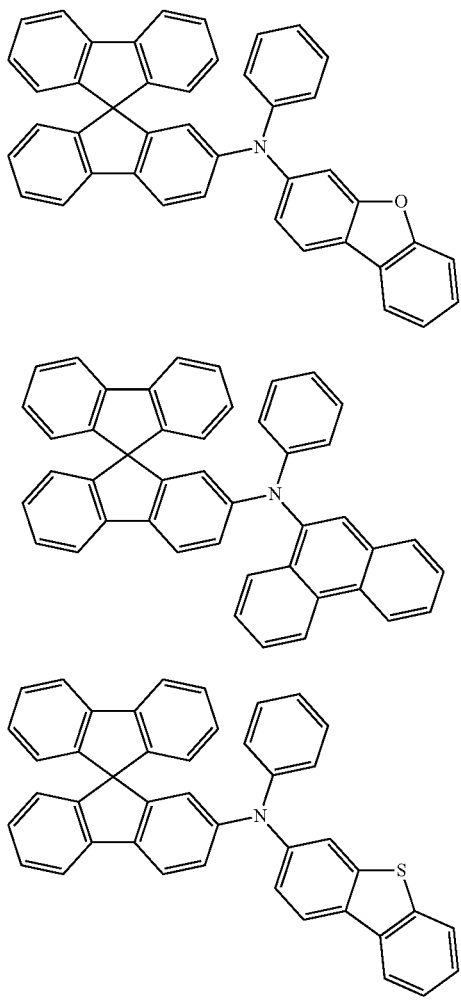

HTL-16

HTL-17

HTL-18

The energy level of the triplet state of the first host 232 and the hole transporting material were measured and listed in Table 1.

TABLE 1

| HTL-1 | 2.7 eV | HH-1 | 2.8 eV |
|---|---|---|---|
| HTL-2 | 2.8 eV | HH-2 | 2.8 eV |
| HTL-3 | 2.8 eV | HH-3 | 2.8 eV |
| HTL-4 | 2.8 eV | HH-4 | 2.7 eV |
| HTL-5 | 2.7 eV | HH-5 | 2.7 eV |
| HTL-6 | 2.6 eV | HH-6 | 2.7 eV |
| HTL-7 | 2.8 eV | HH-7 | 2.8 eV |
| HTL-8 | 2.8 eV | HH-8 | 2.7 eV |
| HTL-9 | 2.8 eV | HH-9 | 2.7 eV |
| HTL-10 | 2.7 eV | HH-20 | 2.8 eV |
| HTL-11 | 2.7 eV | HH-21 | 2.8 eV |
| HTL-12 | 2.6 eV | HH-22 | 2.7 eV |

Since the hole transporting material in the HTL 220 has the energy level of the triplet state being substantially equal to the first host 232 and being higher than the second host 234, the leakage of the exciton, which is generated in the EML 230, into a HTL 220 side is prevented.

Namely, since the first host 232 as a p-type host is a compound including a biscarbazole moiety and one of a dibenzofuran moiety and a dibenzothiophene moiety, in which an aryl group is bonded (connected) to a first position of the one of the dibenzofuran moiety; and the dibenzothiophene moiety, the first host 232 has high energy level of the triplet state. Particularly, it is included in the EML 230 with the green dopant, which has relatively high energy level of the triplet state, it is preferred that the hosts 232 and 234 have a high energy level of the triplet state.

However, the first host 232 having the above-mentioned properties has relatively low hole mobility such that the probability of exciton generation at a boundary of the HTL 220 and the EML 230 is increased. Accordingly, the exciton generated in the EML 230 is leaked into the HTL 220, and thus the emitting efficiency and the lifespan of the OLED D may be decreased.

In the OLED D of the present disclosure, since the hole transporting material in the HTL 220 has the energy level of the triplet state being substantially equal to the first host 232 and being higher than the second host 234, the leakage of the excitors from the EML 230 into a HTL 220 is minimized or prevented.

Figure 3:
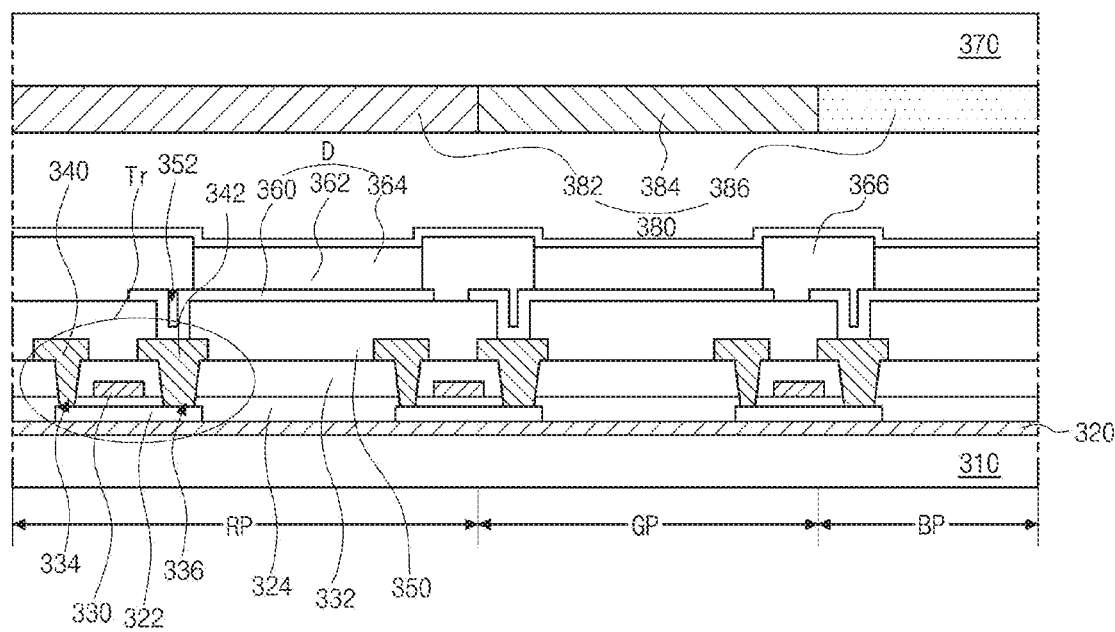
FIG. 3 is a schematic cross-sectional view of an organic light emitting device according to a second embodiment of the present disclosure.
Figure 4:
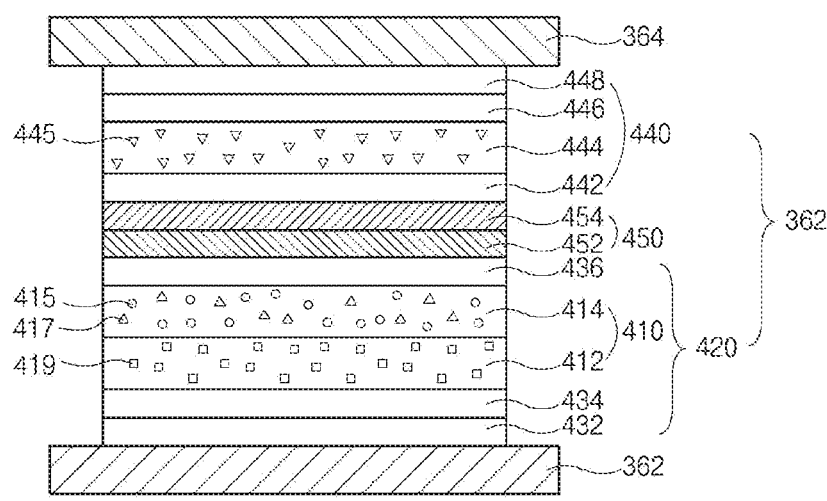
FIG. 4 is a schematic cross-sectional view of an OLED for the organic light emitting device according to the second embodiment of the present disclosure.

FIG. 3 is a schematic cross-sectional view of an organic light emitting device according to a second embodiment of the present disclosure, and FIG. 4 is a schematic cross-sectional view of an OLED for the organic light emitting device according to the second embodiment of the present disclosure.

As shown in FIG. 3, an organic light emitting device 300 includes a first substrate 310, where a red pixel RP, a green pixel GP and a blue pixel BP are defined, a second substrate 370, which faces the first substrate 310, an OLED D between the first and second substrates 310 and 370 and a color filter layer 380 between the OLED D and the second substrate 370. The OLED D provides white light toward the color filter layer 380.

Each of the first and second substrates 310 and 370 may be a glass substrate or a plastic substrate. For example, each of the first and second substrates 310 and 370 may be a polyimide substrate.

A buffer layer 320 is formed on the substrate, and a thin film transistor (TFT) Tr is formed on the buffer layer 320 in each of the red, green and blue pixels RP, GP and BP. The buffer layer 320 may be omitted.

A semiconductor layer 322 formed on the buffer layer 320. The semiconductor layer 322 may include an oxide semiconductor material or polycrystalline silicon.

A gate insulating layer 324 is formed on the semiconductor layer 322. The gate insulating layer 324 may be formed of an inorganic insulating material such as silicon oxide or silicon nitride.

A gate electrode 330, which is formed of a conductive material, e.g., metal, is formed on the gate insulating layer 324 to correspond to a center of the semiconductor layer 322.

An interlayer insulating layer 332, which is formed of an insulating material, is formed on the gate electrode 330. The interlayer insulating layer 332 may be formed of an inorganic insulating material, e.g., silicon oxide or silicon nitride, or an organic insulating material, e.g., benzocyclobutene or photo-acryl.

The interlayer insulating layer 332 includes first and second contact holes 334 and 336 exposing both sides of the semiconductor layer 322. The first and second contact holes 334 and 336 are positioned at both sides of the gate electrode 330 to be spaced apart from the gate electrode 330.

A source electrode 340 and a drain electrode 342, which are formed of a conductive material, e.g., metal, are formed on the interlayer insulating layer 332.

The source electrode 340 and the drain electrode 342 are spaced apart from each other with respect to the gate electrode 330 and respectively contact both sides of the semiconductor layer 322 through the first and second contact holes 334 and 336.

The semiconductor layer 322, the gate electrode 330, the source electrode 340 and the drain electrode 342 constitute the TFT Tr. The TFT Tr serves as a driving element.

The gate line and the data line cross each other to define the pixel region, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A passivation layer 350, which includes a drain contact hole 352 exposing the drain electrode 342 of the TFT Tr, is formed to cover the TFT Tr.

A first electrode 360, which is connected to the drain electrode 342 of the TFT Tr through the drain contact hole 352, is separately formed in each pixel. The first electrode 360 may be an anode and may be formed of a conductive material having a relatively high work function. For example, the first electrode 360 may be formed of a transparent conductive material such as ITO or IZO.

A bank layer 366 is formed on the passivation layer 350 to cover an edge of the first electrode 360. Namely, the bank layer 366 is positioned at a boundary of the pixel and exposes a center of the first electrode 360 in the pixel. The bank layer 366 may be omitted.

An organic emitting layer 362 is formed on the first electrode 360, and a second electrode 364 is formed on the organic emitting layer 362 and the bank layer 366. The second electrode 364 corresponds to the red, green and blue pixels Rp, Gp and Bp.

The second electrode 364 may be formed of a conductive material having a relatively low work function to serve as a cathode. For example, the second electrode 164 may be formed of aluminum (Al), magnesium (Mg) or Al—Mg alloy.

When the OLED D is a top-emission type, a reflection electrode or a reflection layer may be formed under the first electrode 360. For example, the reflection electrode or the reflection layer may be formed of aluminum-palladium-copper (APC) alloy. In this instance, the second electrode 364 has a thin profile such that the light from the emitting layer 362 passes through the second electrode 364.

When the OLED D is a bottom-emission type, there is no reflection electrode or a reflection layer under the first electrode 360, and the second electrode 364 may have a thick profile to be a reflective electrode.

Referring to FIG. 4, the organic emitting layer 362 includes a first emitting part 420 including a first EML 410, a second emitting part 440 including a second EML 444 and a charge generation layer (CGL) 450 between the first and second emitting parts 420 and 440.

The CGL 450 is positioned between the first and second emitting parts 420 and 440. Namely, the first emitting part 420, the CGL 450 and the second emitting part 440 are sequentially stacked on the first electrode 360. In other words, the first emitting part 420 is positioned between the first electrode 360 and the CGL 450, and the second emitting part 440 is positioned between the second electrode 364 and the CGL 450.

The first emitting part 420 may include a first EML 410 and a first HTL 434 between the first electrode 360 and the first EML 410. In addition, the first emitting part 420 may further include an HIL 432 between the first electrode 360 and the first HTL 434, a first ETL 436 between the first EML 410 and the CGL 450.

The first EML 410 includes a lower EML 412 and an upper EML 414. For example, the lower EML 412 may be a red EML, and the upper EML 414 may be a green EML. Alternatively, the lower EML 412 may be a green EML, and the upper EML 414 may be a red EML. Namely, the first EML 410 has a double-layered structure including a green EML and a red EML.

The upper EML 414 as the green EML includes a first host 415 as a p-type host, a second host 417 as an n-type host and a green dopant.

The first host 415 may be represented by the above Formula 1, and the second host 417 may be represented by the above Formula 3-1. The green dopant may be represented by the above Formulas 5-1 or 5-2.

Namely, the first host 415 is a compound including a biscarbazole moiety and one of a dibenzofuran moiety and a dibenzothiophene moiety, in which an aryl group is bonded (connected) to a first position of the one of the dibenzofuran moiety and the dibenzothiophene moiety, and has an energy level of the triplet state in a range of about 2.6 to 2.8 eV. The second host 417 is a compound including a first moiety of triazine and a second moiety of carbazole or dibenzofuran, in which the first and second moieties are connected to each other in direct or through a linker, and has an energy level of a triplet state in a range of 2.4 to 2.8 eV. In addition, the green dopant may be an iridium complex in the above Formulas 5-1 or 5-2.

The energy level of the triplet state of the second host 417 is equal to or lower than that of the first host 415. The energy level of the triplet state of the green dopant is equal to or lower than that of each of the first and second hosts 415 and 417. In addition, a difference between the energy level of the triplet state of the first host 415 and the energy level of the triplet state of the second host 417 may be equal to or less than 0.4 eV.

As a result, the emitting efficiency and the lifespan of the OLED D including the first emitting part 420 are improved.

The lower EML 412 as the red EML includes a host 419 and a red dopant. The host of the lower EML 412 may include the first host of the Formula 1 and the second host of Formula 3-1. Alternatively, the host 419 in the lower EML 412 may be a compound of Formula 8.

[Formula 8]

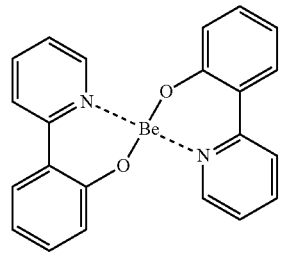

The red dopant may be a compound represented by Formula 9-1 or Formula 9-2, but it is not limited thereto.

[Formula 9-1]

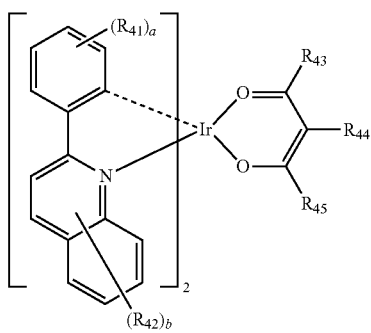

[Formula 9-2]

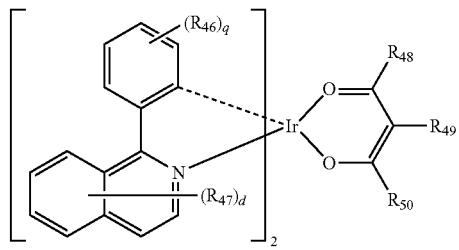

In Formulas 9-1 and 9-2, each of $R_{41}$, $R_{42}$, $R_{46}$ and $R_{47}$ is independently selected from the group consisting of deuterium, halogen, C1 to C10 alkyl, C3 to C10 cycloalkyl, C6 to C30 aryl and C5 to C30 heteroaryl. Each of a and c is independently an integer of 0 to 4, and each of b and d is independently an integer of 0 to 6. Each of $R_{43}$ to $R_{45}$ and $R_{45}$ to $R_{50}$ is independently selected from the group consisting of hydrogen, deuterium and C1 to C10 alkyl.

For example, the red dopant may be one of [bis(2-(4,6-dimethyl)phenylquinoline)](2,2,6,6-tetramethylheptane-3,5-dionate)iridium(III), bis[2-(4-n-hexylphenyl)quinoline]acetylacetonate)iridium(III), tris[2-(4-n-hexylphenyl)quinoline]iridium(III), tris[2-phenyl-4-methylquinoline]iridium(III), bis(2-phenylquinoline)(2,2,6,6-tetramethylheptene-3,5-dionate)iridium(III), bis(phenylisoquinoline)(2,2,6,6-tetramethylheptene-3,5-dionate)iridium(III), bis[(4-n-hexylphenyl)isoquinoline](acetylacetonate)iridium(III), tris[2-(4-n-hexylphenyl)quinoline]iridium(III), tris(2-(3-methylphenyl)-7-methyl-quinolato)iridium, bis[2-(2-methylphenyl)-7-methyl-quinoline](acetylacetonate)iridium(III), and bis[2-(3,5-dimethylphenyl)-4-methyl-quinoline](acetylacetonate)iridium(III)).

The red dopant may have a percentage by weight of about 1 to 15 in the lower EML 412, and the green dopant may have a percentage by weight of about 5 to 25 in the upper EML 414. Namely, the percentage by weight of the green dopant is greater than that of the red dopant.

The first ETL 434 may include a hole transporting material in the above Formula 6. The hole transporting material in the first ETL 434 has an energy level of a triplet state of about 2.4 to 3.0 eV. The energy level of the triplet state of the hole transporting material may be greater than the second host 234. Accordingly, the emitting efficiency and the lifespan of the OLED D including the first emitting part 420 are further improved.

The second emitting part 440 includes a second EML 444. In addition, the second emitting part 440 may further include a second HTL 442 between the CGL 450 and the second EML 444, a second ETL 446 between the second EML 444 and the second electrode 364, and an EIL 448 between the second ETL 446 and the second electrode 364.

The second EML 444 includes a host 445 and a blue dopant. The blue dopant may be a fluorescent dopant or a delayed fluorescent dopant.

For example, the host 445 of the second EML 444 may be 1,3-bis(N-carbazolyl)benzene (mCP), but it is not limited thereto. The blue dopant may be bis[2-(4,6-difluorophenyl)pyridinato-C2,N](picolinato)iridium(III) (Firpic), but it is not limited thereto.

The CGL 450 is positioned between the first emitting part 420 and the second emitting part 440. Namely, the first and second emitting parts 420 and 440 are connected by the CGL 450. The CGL 450 may be a P-N junction type CGL including an N-type CGL 452 and a P-type CGL 454.

The N-type CGL 452 is positioned between the first ETL 436 and the second HTL 442, and the P-type CGL 454 is positioned between the N-type CGL 452 and the second HTL 442.

In the OLED D of the present disclosure, the red light and the green light are emitted from the first emitting part 420, and the blue light is emitted from the second emitting part 440. As a result, the white light is provided from the OLED D.

In the first emitting part 420, the lower EML 412 and the upper EML 414 may be sequentially (or continuously) formed by a deposition process. Accordingly, the OLED D of the present disclosure has a double-stack structure. Namely, the lower EML 412 and the upper EML 414 contact each other. Alternatively, the lower EML 412 as the red EML and the upper EML 414 as the green EML may be disposed in different emitting parts such that the OLED D may have a triple-stack structure. In this instance, a CGL may be disposed between the lower and upper EMLs 412 and 414.

Referring again to FIG. 3, the color filter layer 380 is positioned on or over the OLED D and includes a red color filter pattern 382, a green color filter pattern 384 and a blue color filter pattern 386 respectively corresponding to the red pixel RP, the green pixel GP and the blue pixel BP.

The color filter layer 380 may be attached to the OLED D by an adhesive layer. Alternatively, the color filter layer 380 may be directly formed on the OLED D.

In addition, an encapsulation film may be formed to cover the OLED D to prevent penetration of moisture into the OLED D. For example, the encapsulation film may include a first inorganic insulating layer, an organic insulating layer and a second inorganic insulating layer sequentially stacked, but it is not limited thereto. The encapsulation film may be omitted.

Moreover, a polarization plate for reducing an ambient light reflection may be disposed at an outer side of the second substrate 370. For example, the polarization plate may be a circular polarization plate. The polarization plate may be omitted.

In FIG. 3, the light from the OLED D is provided through the second electrode 364, and the color filter layer 380 is disposed over the OLED D. Alternatively, the light from the OLED D may be provided through the first electrode 360, and the color filter layer 380 may be disposed between the OLED D and the first substrate 310.

In addition, a color conversion layer may be disposed between the OLED D and the color filter layer 380. The color conversion layer may include a red color conversion layer, a green color conversion layer and a blue color conversion layer respectively corresponding to the red pixel RP, the green pixel GP and the blue pixel BP such that the white light from the OLED D may be converted into the red light, the green light and the blue light in the red pixel RP, the green pixel GP and the blue pixel BP.

The white light from the OLED D passes through the red color filter pattern 382 in the red pixel RP, the green color filter pattern 384 in the green pixel GP and the blue color filter pattern 386 in the blue pixel such that the red light, the green light and the blue light are provided from the red pixel RP, the green pixel OP and the blue pixel BP, respectively.

In FIG. 3, the OLED D emitting the white light is driven in each pixel such that the organic light emitting device 300 is used as a display device. Alternatively, the OLED D is formed on an entire surface of the substrate without a driving element, e.g., the TFT Tr, and the color filter layer 380 such that the organic light emitting device may be used as a lightening device.

[OLED]

On an anode (ITO), an HIL (Formula 10, 50 Å), an HTL (200 Å), a red EML (host (Formula 11, 97 wt %)+dopant (Formula 12, 3 wt %), 200 Å), a green EML (host (85 wt %)+dopant (Formula 13, 15 wt %), 300 Å), an ETL (Formula 14, 200 Å), an EIL (LiF, 10 Å), and a cathode (Al, 1000 Å) are sequentially stacked such that the OLED is manufactured.

1. Example 1 (Ex1)

The compound HTL-1 of Formula 7 is used to form the HTL, and the compound HH-1 of Formula 2 and the compound EH-1 of Formula 4 (a weight ratio–1:1) are used as the host to form the green EML.

2. Comparative Example 1 (Ref1)

The compound of Formula 15 is used instead of the compound HTL-1 in Example 1, and the compound of formula 16 is used instead of the compound HH-1 in Example 1.

[Formula 10]

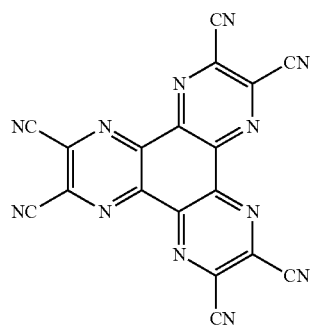

[Formula 11]

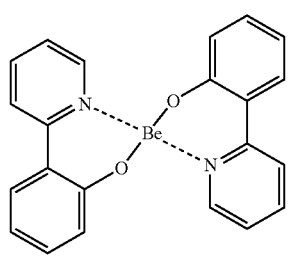

[Formula 12]

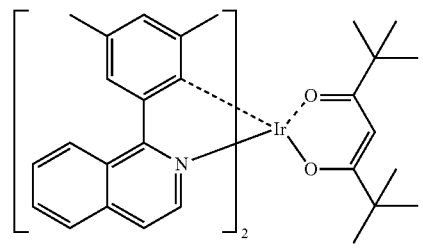

[Formula 13]

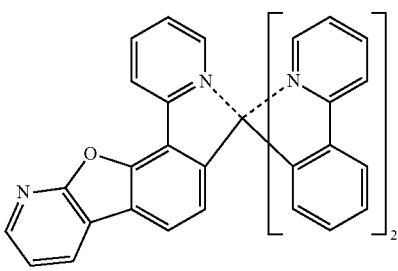

[Formula 14]

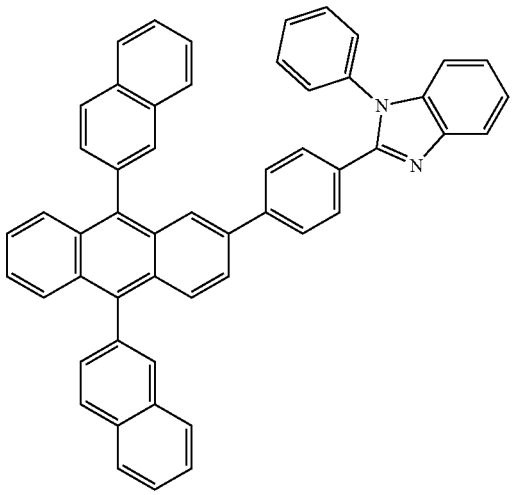

[Formula 15]

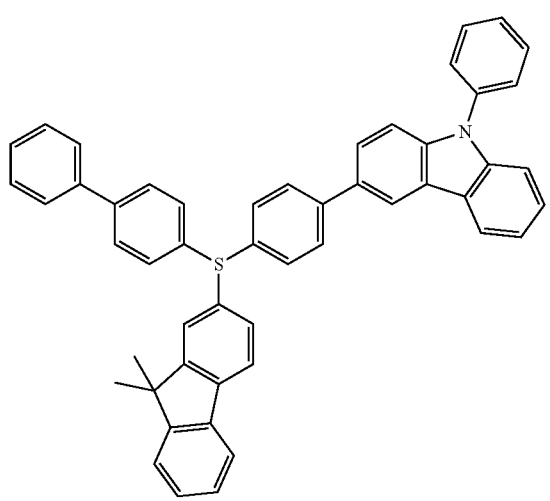

[Formula 16]

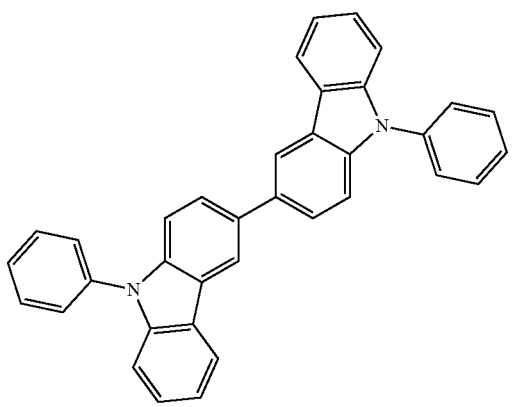

-continued

The properties, e.g., voltage (V), efficiency (cd/A), external quantum efficiency (EQE), color coordinate index (CIE) and lifespan (LT), of the OLED in Example 1 and Comparative Example 1 are measured and listed in Table 2 and shown in FIGS. 5A to 5D

TABLE 2

| | V | Cd/A | EQE [%] | CIE x | CIE y | LT (@50 mA/cm$^2$) |
|---|---|---|---|---|---|---|
| Ex1 | 4.0 | 46.0 | 20.1 | 0.445 | 0.535 | 110% |
| Ref1 | 3.9 | 45.8 | 19.5 | 0.441 | 0.540 | 100% |

Figure 5A:
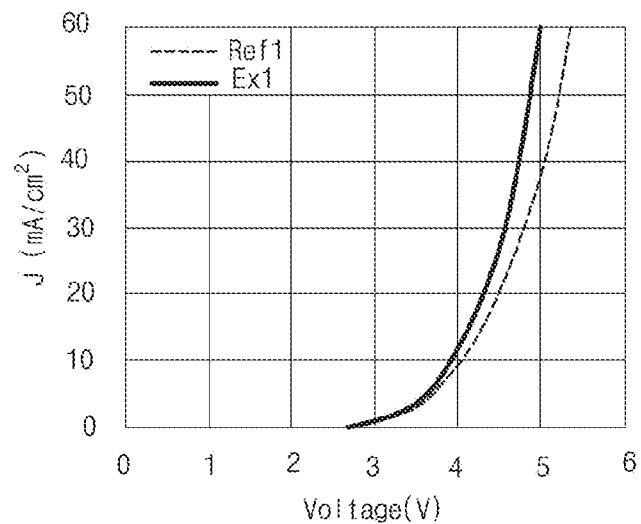
FIGS. 5A to 5D and FIGS. 6A to 6D are graphs showing properties of an OLED of the present disclosure.
Figure 5B:
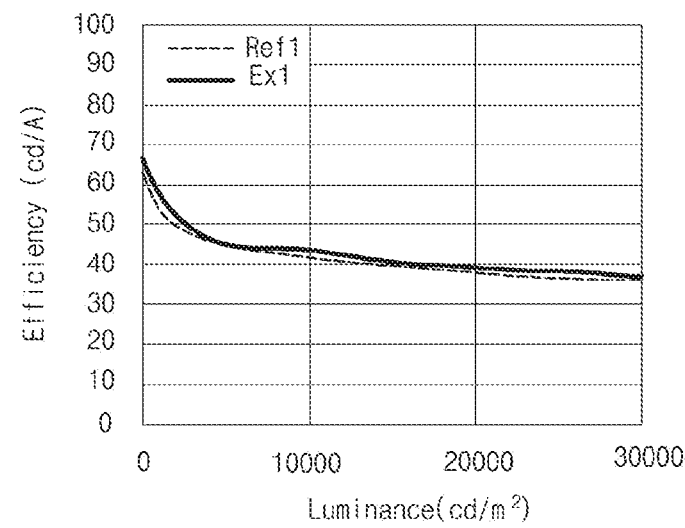
Figure 5C:
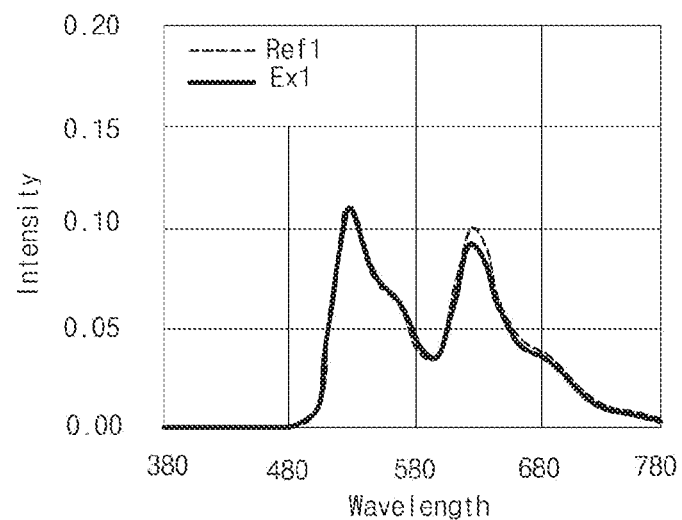
Figure 5D:
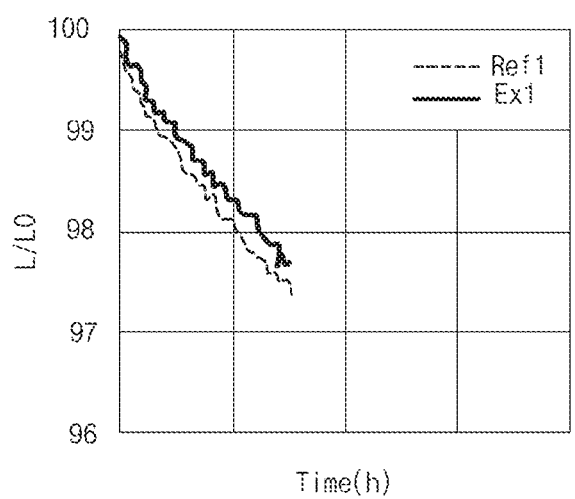

As shown in Table 2 and FIGS. 5A to 5D, in the OLED, where the HTL includes a hole transporting material of the above Formula 6 and the EML includes a first host of the above Formula 1, the emitting efficiency and the lifespan are improved. In addition, even when the OLED has a single-stack structure by sequentially stacking the red EML and the green EML, the red light and the green light having substantially same brightness are emitted. FIG. 5A is a graph of voltage (V) vs. lifespan (mA/cm$^2$) for Example 1 and Comparative Example 1. FIG. 5B is a graph of luminance (cd/m$^2$) vs. efficiency (cd/A) for Example 1 and Comparative Example 1. FIG. 5C is a graph of wavelength vs. intensity for Example 1 and Comparative Example 1. FIG. 5D is a graph of time (h) vs lifespan ratio to initial lifespan (L0).

[OLED]

On an anode (ITO), an HIL (Formula 10, 50 Å), an HTL (200 Å), an EML (host (85 wt %)+dopant (Formula 13, 15 wt %), 300 Å), an ETL (Formula 14, 200 Å), an EIL (LiF, 10 Å), and a cathode (Al, 1000 Å) are sequentially stacked such that the OLED is manufactured.

1. Example 2 (Ex2)

The compound HTL-1 of Formula 7 is used to form the HTL, and the compound HH-1 of Formula 2 and the compound EH-1 of Formula 4 (a weight ratio=1:1) are used as the host to form the EML.

2. Comparative Example 2 (Ref2)

The compound of Formula 15 is used instead of the compound HTL-1 in Example 1, and the compound of formula 16 is used instead of the compound HH-1 in Example 1.

The properties, e.g., voltage (V), efficiency (cd/A), external quantum efficiency (EQE), color coordinate index (CIE) and lifespan (LT), of the OLED in Example 2 and Comparative Example 2 are measured and listed in Table 3 and shown in FIGS. 6A to 6D.

TABLE 3

| | V | Cd/A | EQE [%] | CIE x | CIE y | LT (@50 mA/cm$^2$) |
|---|---|---|---|---|---|---|
| Ex2 | 3.2 | 61.7 | 15.9 | 0.346 | 0.627 | 130% |
| Ref2 | 3.1 | 57.3 | 14.9 | 0.356 | 0.619 | 100% |

Figure 6A:
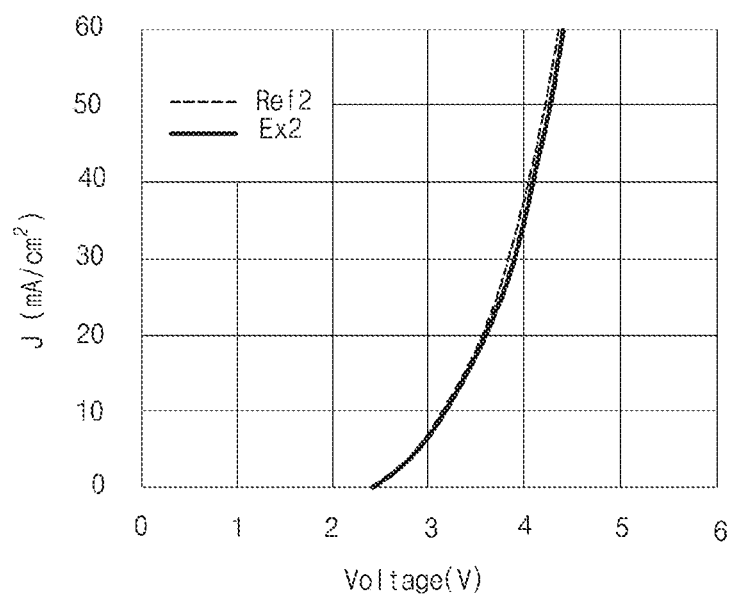
Figure 6B:
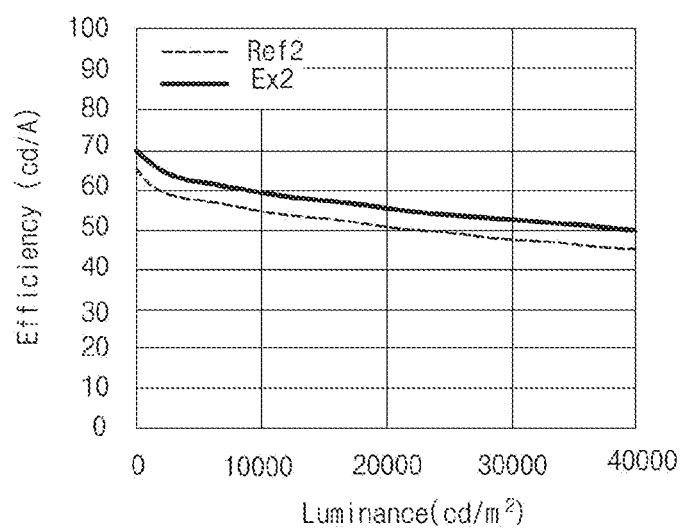
Figure 6C:
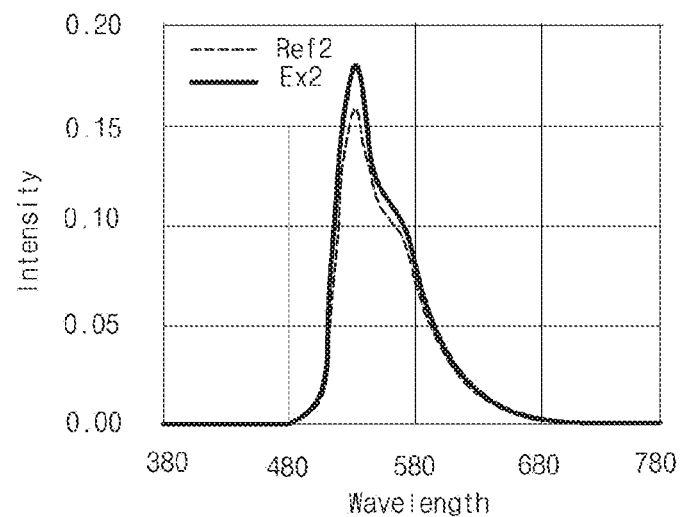
Figure 6D:
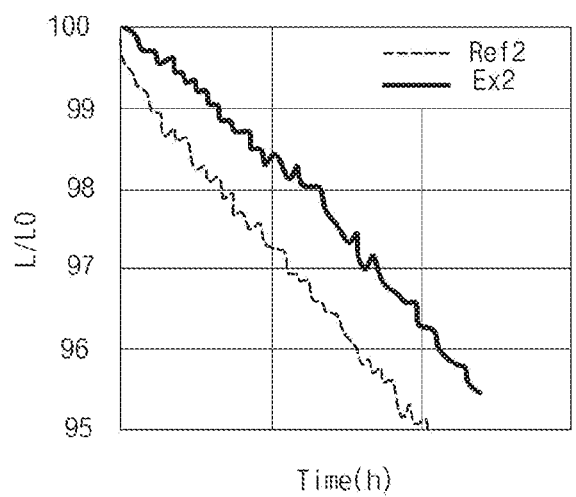

As shown in Table 3 and FIGS. 6A to 6D, in the OLED, where the HTL includes a hole transporting material of the above Formula 6 and the EML includes a first host of the above Formula 1, the emitting efficiency and the lifespan are improved. FIG. 6A is a graph of voltage (V) vs. lifespan (mA/cm$^2$) for Example 2 and Comparative Example 2. FIG. 6B is a graph of luminance (cd/m$^2$) vs. efficiency (cd/A) for Example 2 and Comparative Example 2. FIG. 6C is a graph of wavelength vs. intensity for Example 2 and Comparative Example 2. FIG. 6D is a graph of time (h) vs lifespan ratio to initial lifespan (L0).

As mentioned above, in the OLED of the present disclosure, the EML includes the first host, which is a compound including a biscarbazole moiety and one of a dibenzofuran moiety and a dibenzothiophene moiety, in which an aryl group is bonded (connected) to a first position of the one of the dibenzofuran moiety and the dibenzothiophene moiety, and the HTL includes a hole transporting material, which is an aromatic amine compound substituted by spiro-fluorene group. Accordingly, the emitting efficiency and the lifespan of the OLED are significantly improved.

It will be apparent to those skilled in the art that various modifications and variations can be made in the present disclosure without departing from the spirit or scope of the present disclosure. Thus, it is intended that the present disclosure cover the modifications and variations of the present disclosure provided they come within the scope of the appended claims and their equivalents.

What is claimed is:

1. An organic light emitting diode, comprising:
   a first electrode;
   a second electrode facing the first electrode; and
   a first emitting material layer including a first host, a second host and a first dopant, and disposed between the first and second electrodes, wherein the first host is represented by Formula 1:

[Formula 1]

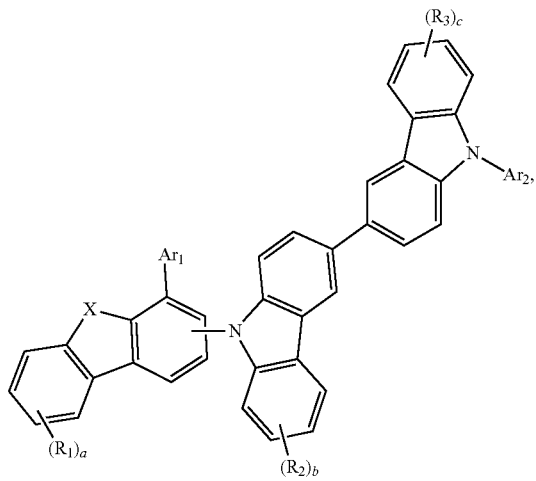

wherein X is O or S,
wherein Ar$_1$ is C10 to C30 aryl, and Ar$_2$ is C6 to C30 aryl,
wherein each of R$_1$ to R$_3$ is independently selected from the group consisting of halogen, C1 to C10 alkyl, C1 to C20 aryl and C3 to C10 cycloalkyl, and
wherein each of a, b and c is independently an integer of 0 to 4.

2. The organic light emitting diode according to claim 1, wherein the first host is selected from Formula 2:

[Formula 2]

HH-1

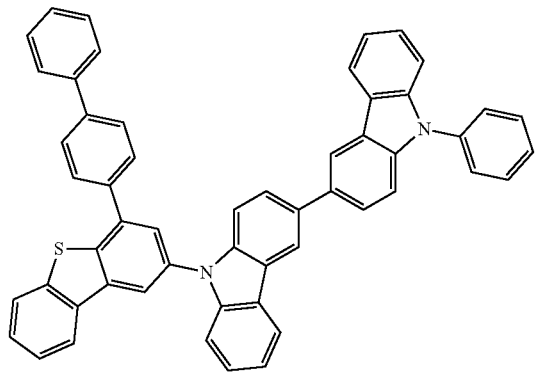

HH-2

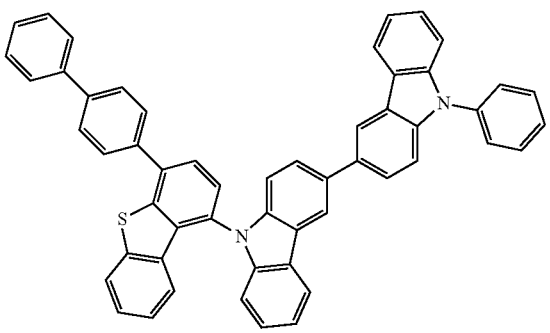

-continued

HH-3

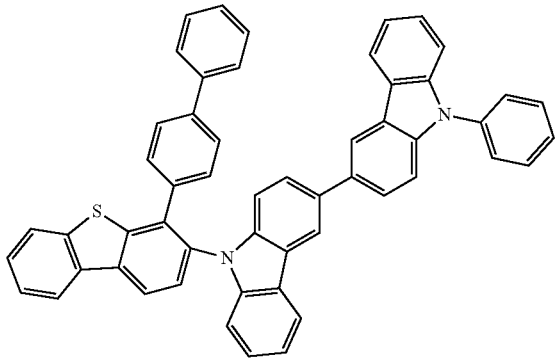

HH-4

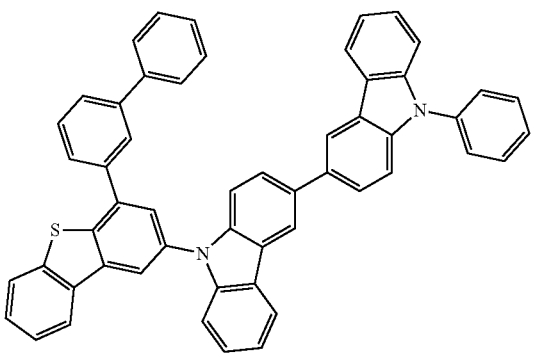

HH-5

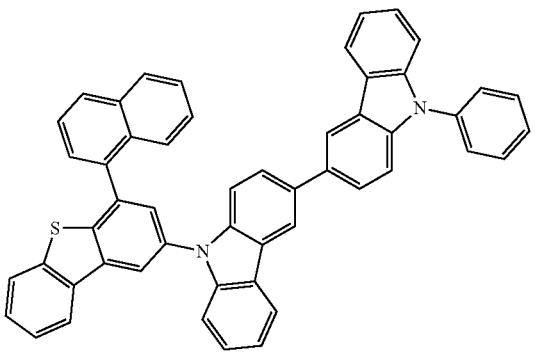

HH-6

HH-7
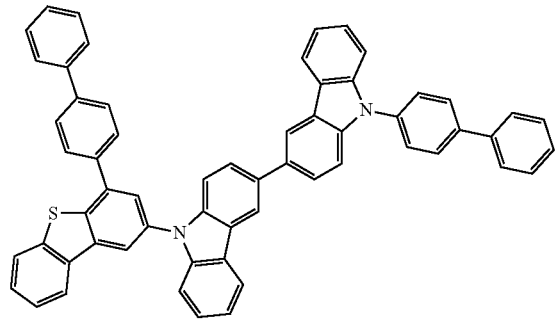
HH-11
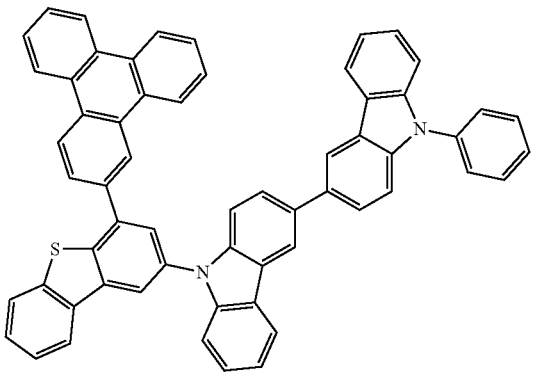
HH-8
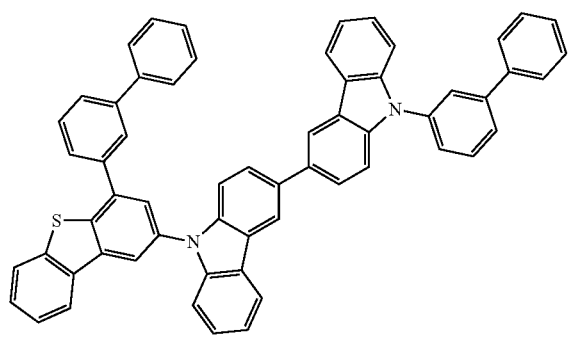
HH-12
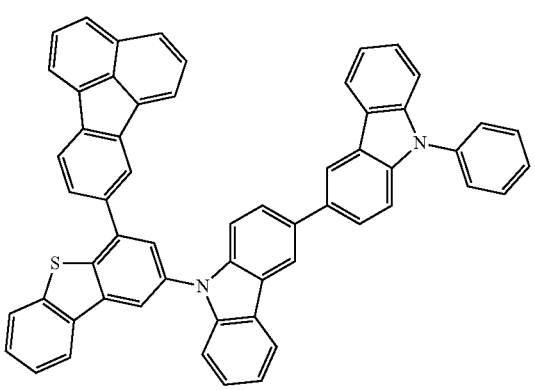
HH-9
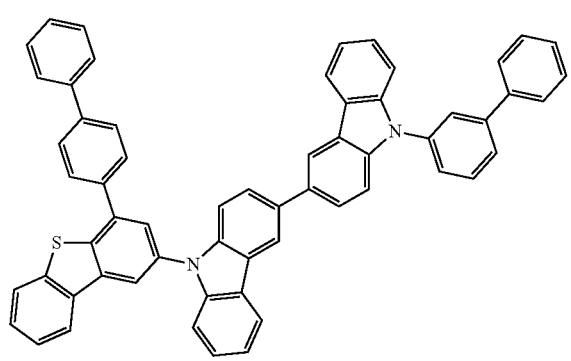
HH-13
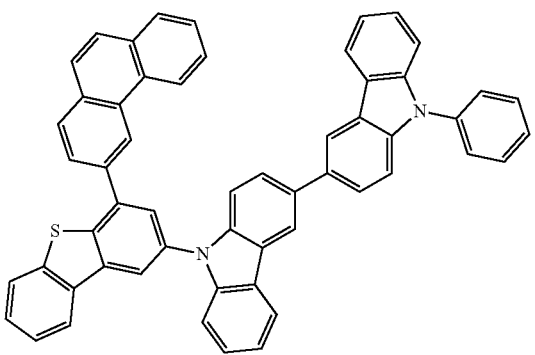
HH-10
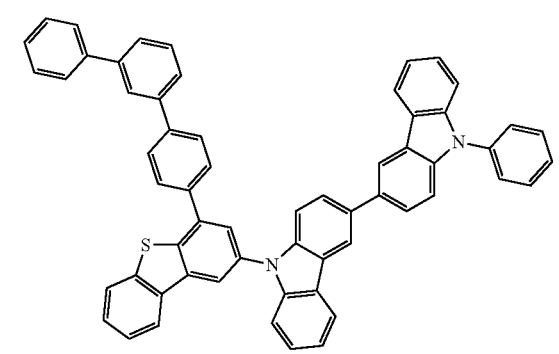
HH-14
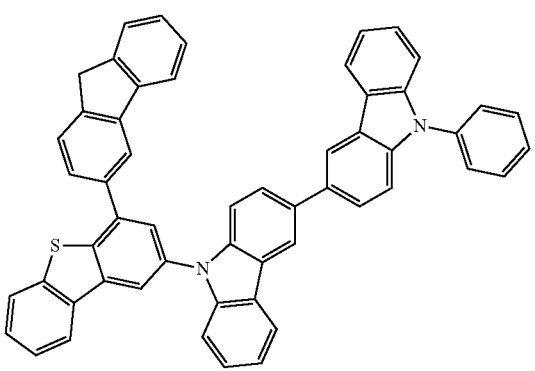

HH-15
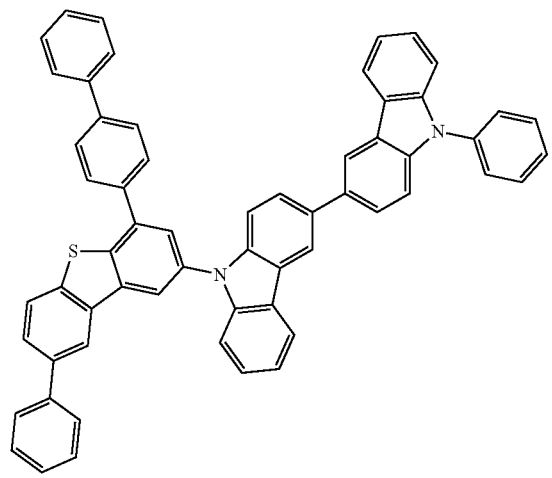
HH-16
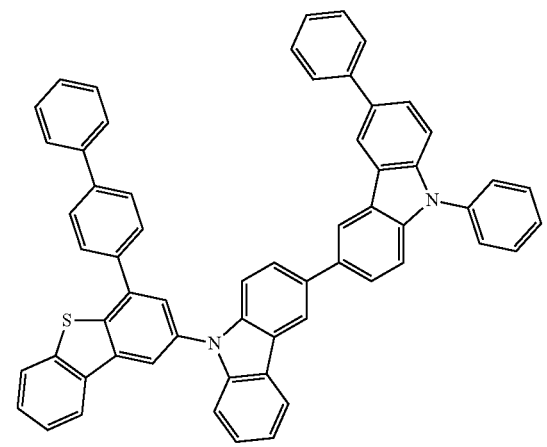
HH-17
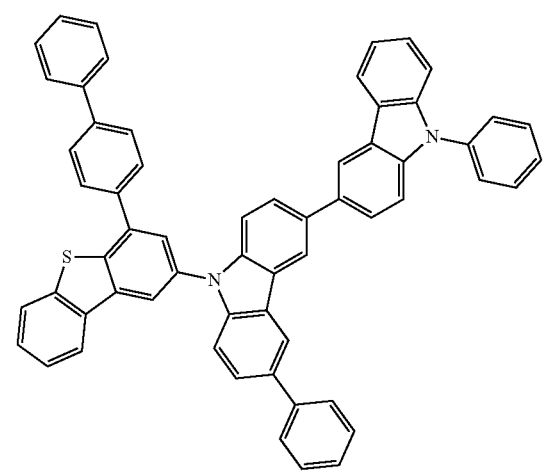
HH-18
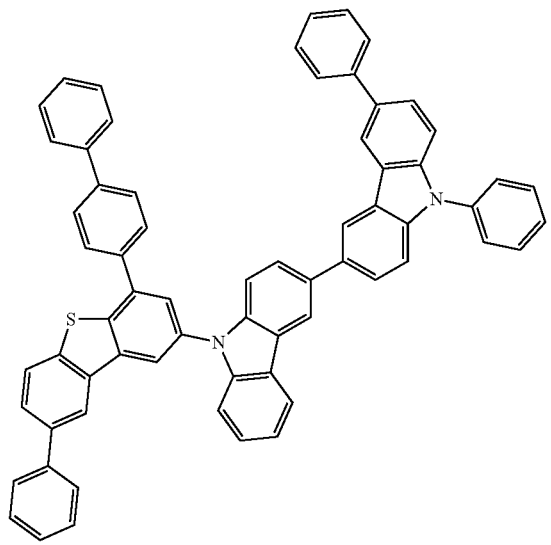
HH-19
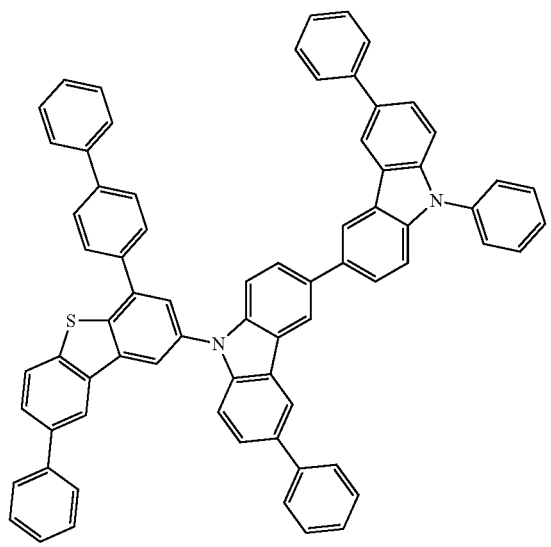
HH-20
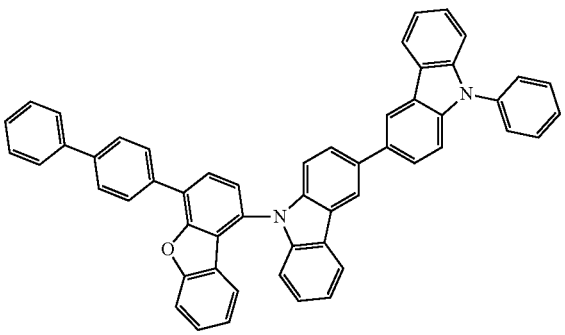

HH-21
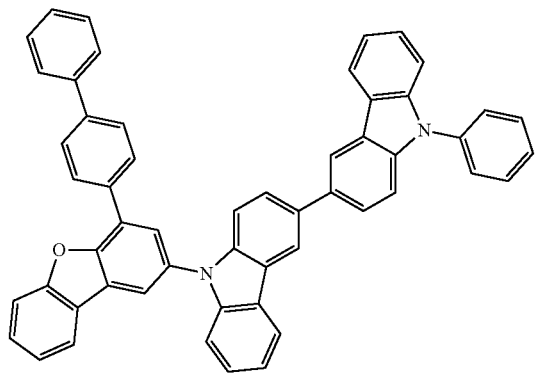
HH-22
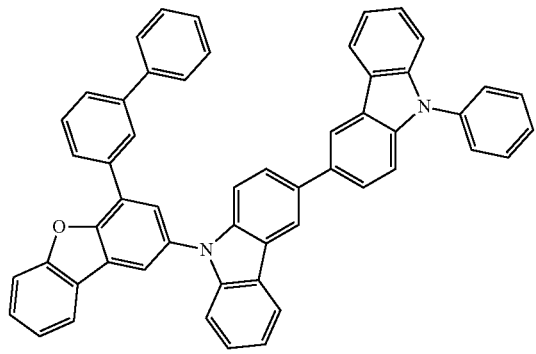
HH-23
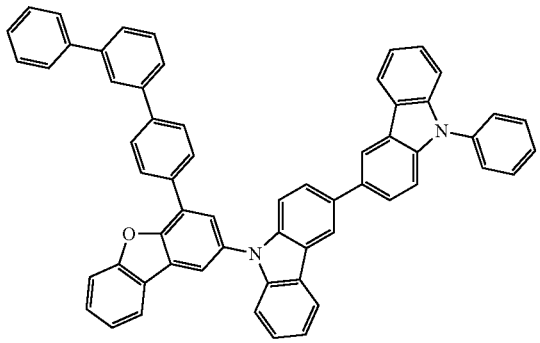
HH-24
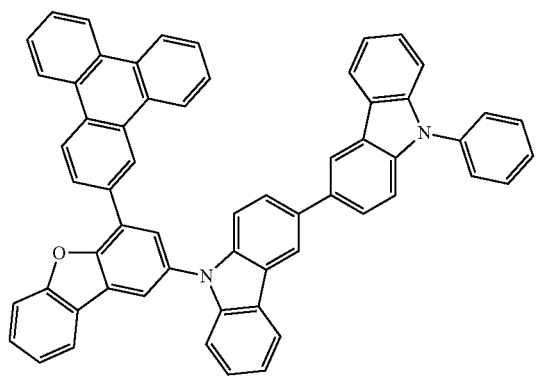
HH-25
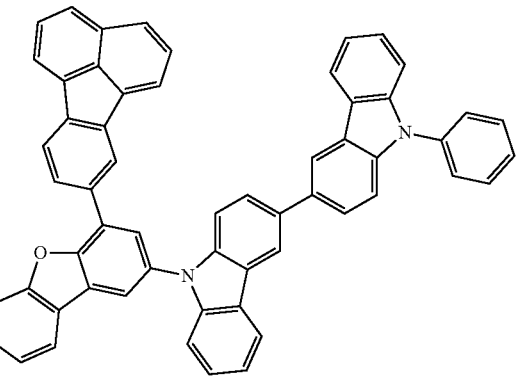
HH-26
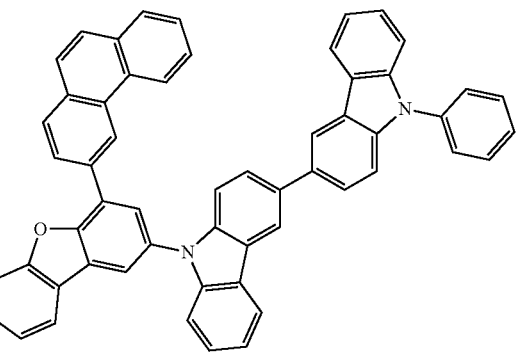
HH-27
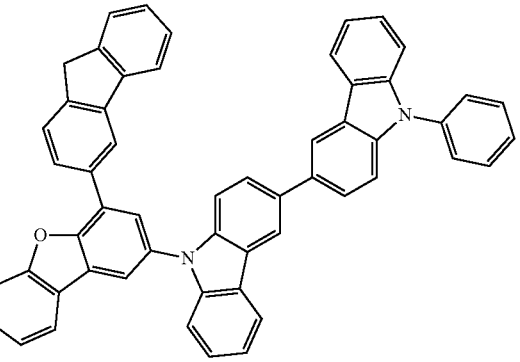
HH-28
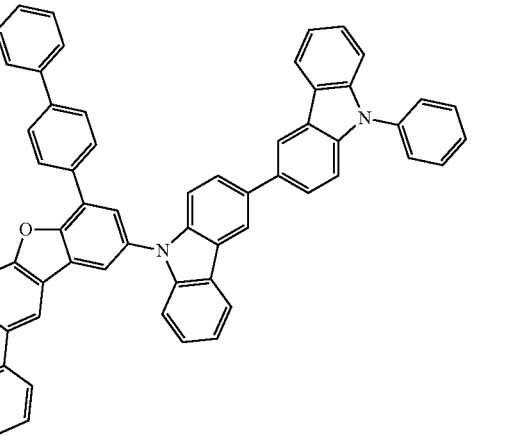

HH-29

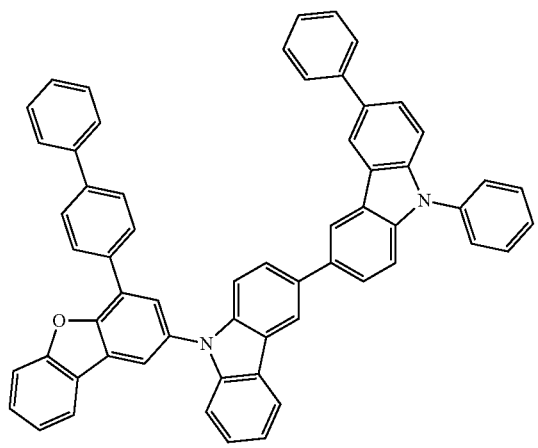

HH-30

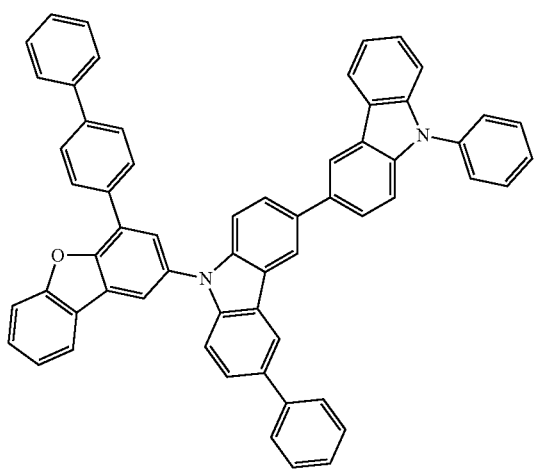

HH-31

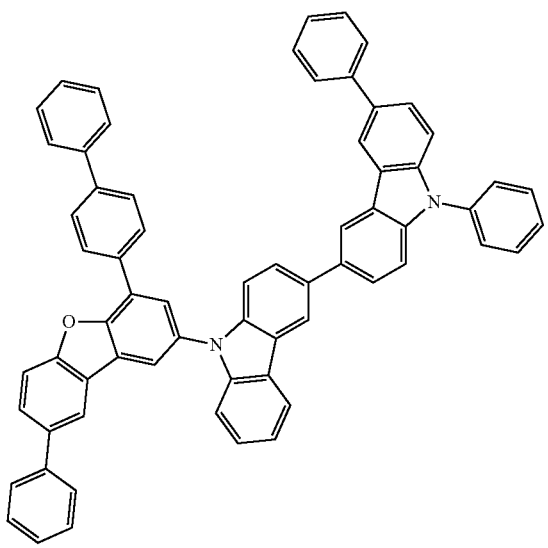

HH-32

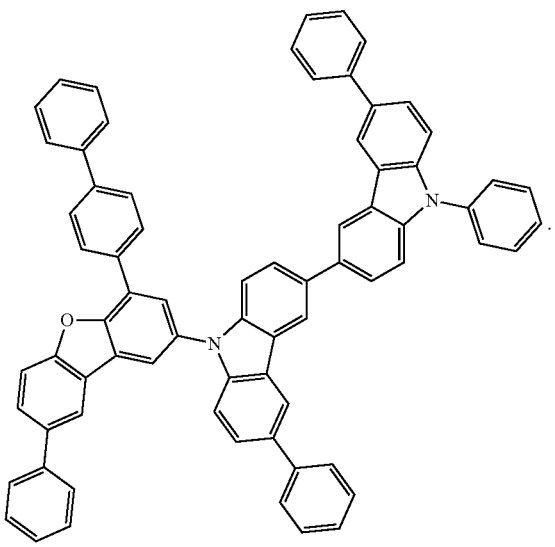

3. The organic light emitting diode according to claim 1, wherein the second host is represented by Formula 3-1:

[Formula 3-1]

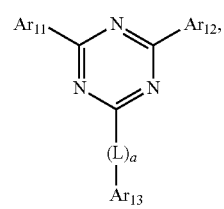

wherein each of $Ar_{11}$ and $Ar_{12}$ is independently selected from the group consisting of hydrogen and C6 to C30 aryl, wherein L is C6 to C30 arylene group, and a is 0 or 1, wherein $Ar_{13}$ is represented by Formula 3-2 or Formula 3-3:

[Formula 3-2]

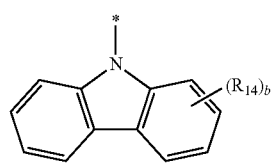

[Formula 3-3]

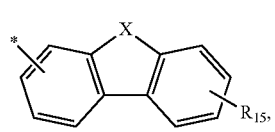

wherein in Formula 3-2, $R_{14}$ is a heteroaryl, or adjacent two $R_{14}$ form a fused ring, wherein h is an integer of 0 to 4, and wherein in Formula 3-3, $R_{15}$ is a heteroaryl, and X is O or S.

4. The organic light emitting diode according to claim 3, wherein the second host is selected from Formula 4:

[Formula 4]

EH-1

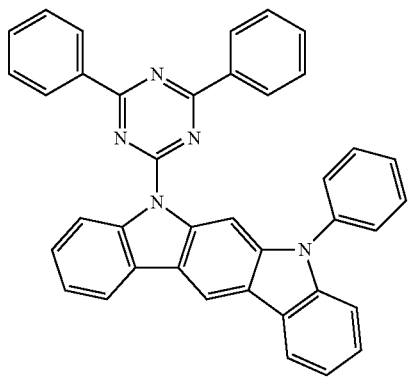

EH-2

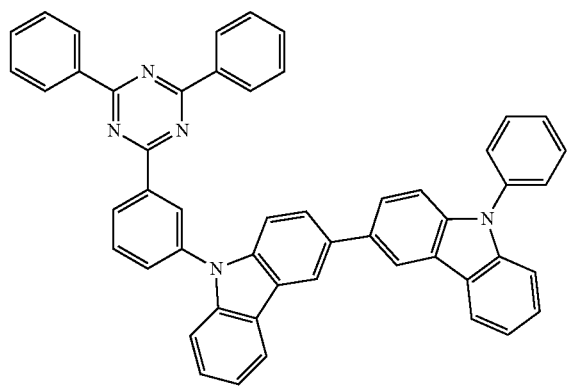

EH-3

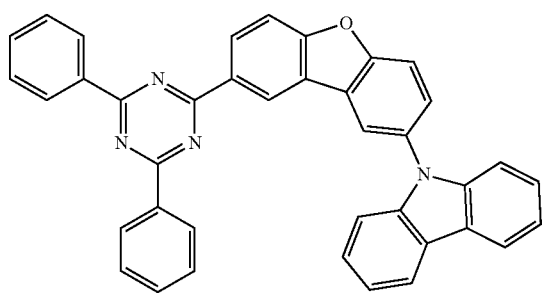

EH-4

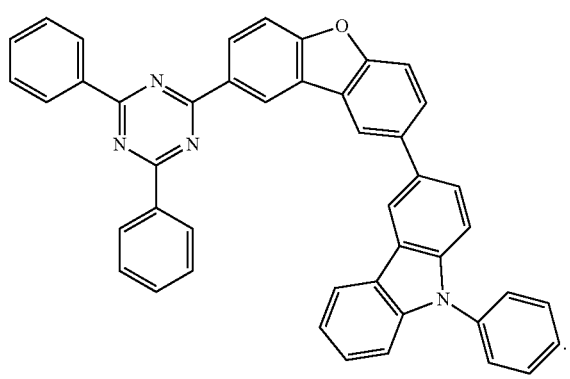

5. The organic light emitting diode according to claim 3, wherein an energy level of a triplet state of the second host is equal to or lower than an energy level of a triplet state of the first host.

6. The organic light emitting diode according to claim 3, wherein a percentage by weight of the first host is equal to or greater than a percentage by weight of the second host.

7. The organic light emitting diode according to claim 1, further comprising:
a hole transporting layer disposed between the first electrode and the first emitting material layer and including a hole transporting material of Formula 6:

[Formula 6]

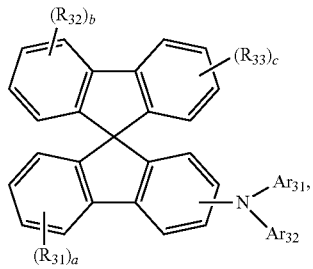

wherein each of $R_{31}$ to $R_{33}$ is independently selected from the group consisting of deuterium, halogen, C1 to C10 alkyl, C3 to C10 cycloalkyl, C6 to C30 aryl, C5 to C30 heteroaryl, trialkylsilyl and triarylsilyl, and each of $Ar_{31}$ and $Ar_{32}$ is independently selected from the group consisting of C6 to C30 aryl and C5 to C30 heteroaryl, and wherein each of a, b and c is independently an integer of 0 to 4.

8. The organic light emitting diode according to claim 7, wherein the hole transporting material is selected from Formula 7:

[Formula 7]

HTL-1

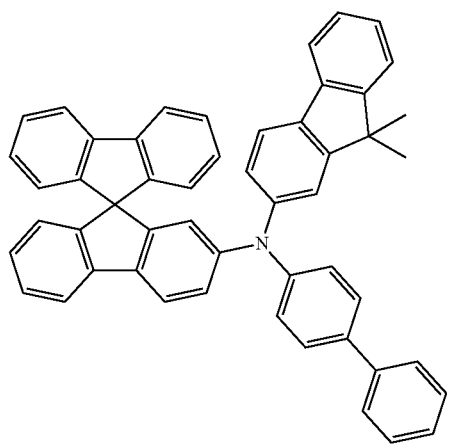

HTL-2
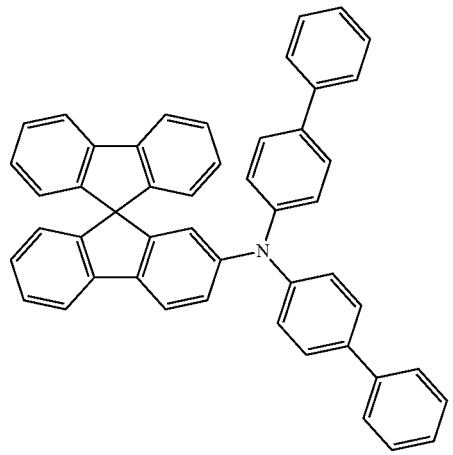
HTL-3
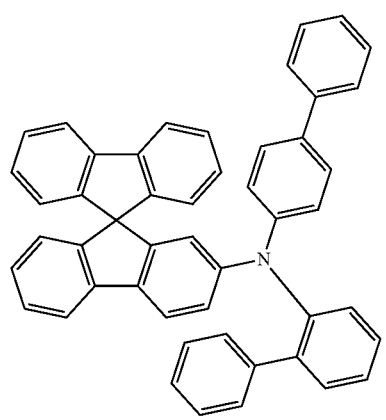
HTL-4
HTL-5
HTL-6
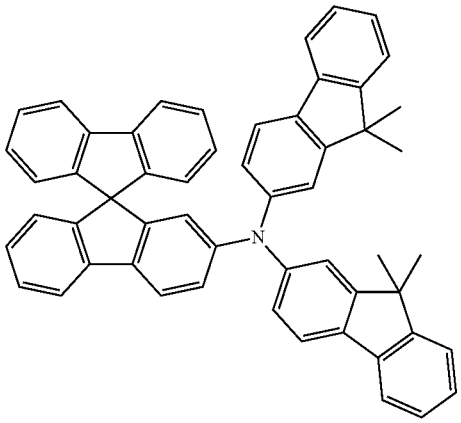
HTL-7
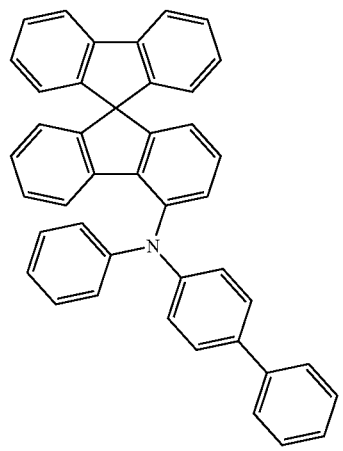
HTL-8
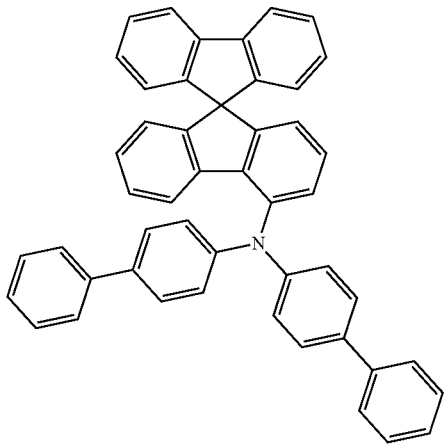

HTL-9
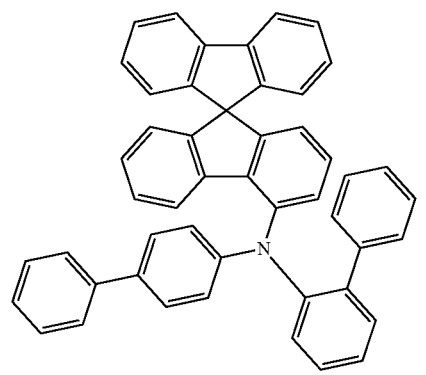
HTL-10
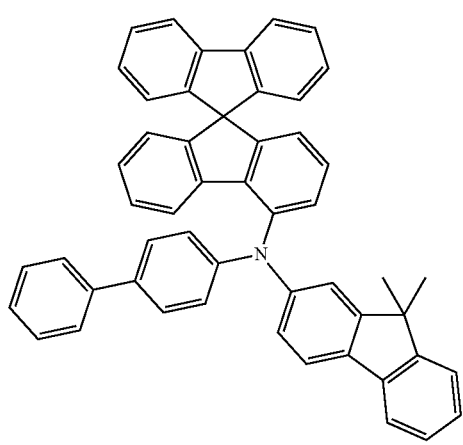
HTL-11
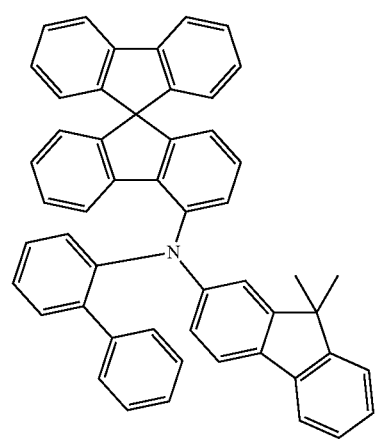
HTL-12
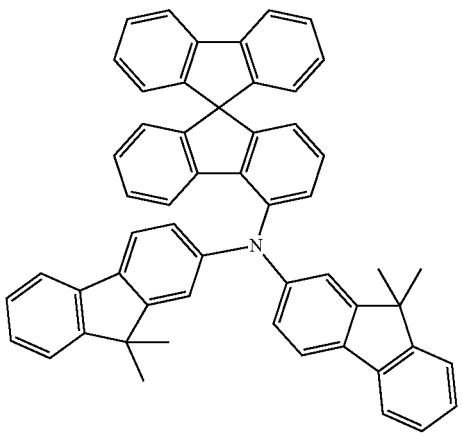
HTL-13
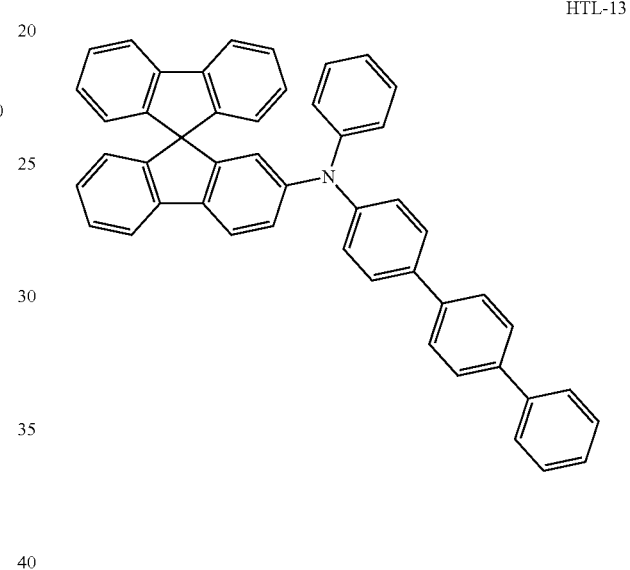
HTL-14
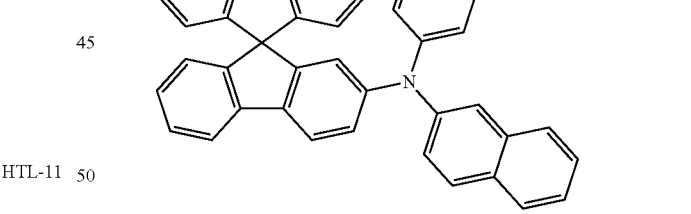
HTL-15
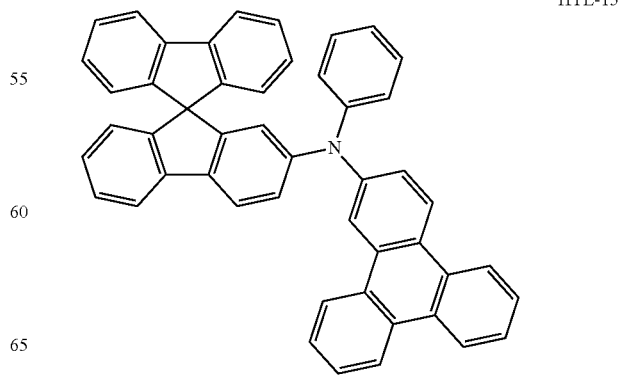

-continued

HTL-16

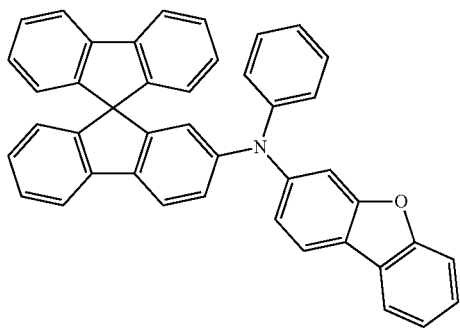

HTL-17

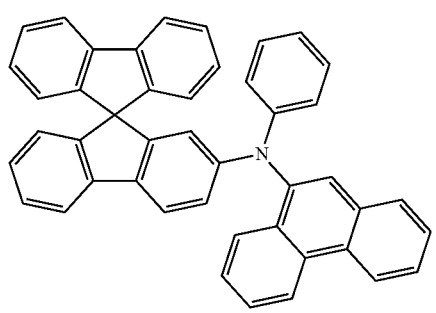

HTL-18

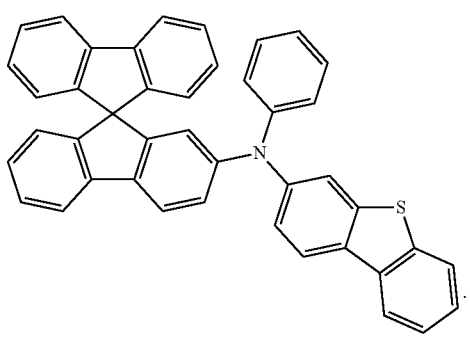

9. The organic light emitting diode according to claim 7, wherein the first host has an energy level of a triplet state of 2.6 to 2.8 eV, and the second host has an energy level of a triplet state of 2.4 to 2.8 eV, and wherein the hole transporting material has an energy level of a triplet state of 2.4 to 3.0 eV.

10. The organic light emitting diode according to claim 1, wherein the first dopant is a green dopant.

11. The organic light emitting diode according to claim 10, further comprising:

a second emitting material layer including a third host and a blue dopant and disposed between the first emitting material layer and the second electrode;

a charge generation layer disposed between the first and second emitting material layers; and a third emitting material layer including a fourth host and a red dopant, the third emitting material layer disposed between the first electrode and the first emitting material layer or between the first emitting material layer and the charge generation layer.

12. The organic light emitting diode according to claim 11, wherein the first and third emitting material layers contact each other.

13. An organic light emitting device, comprising:

a substrate; and an organic light emitting diode on or over the substrate, the organic light emitting diode comprising:

a first electrode;

a second electrode facing the first electrode; and a first emitting material layer including a first host, a second host and a first dopant and disposed between the first and second electrodes, wherein the first host is represented by Formula 1:

[Formula 1]

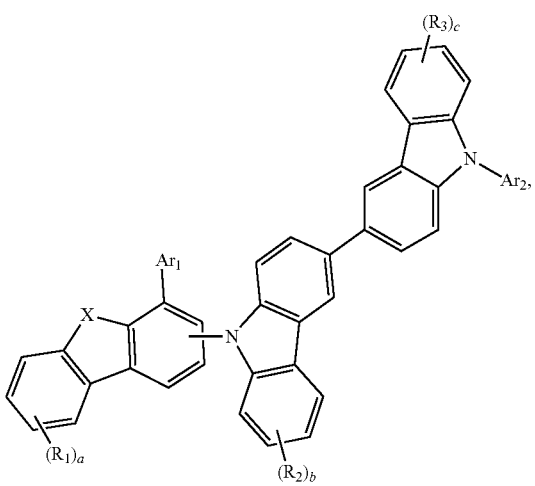

wherein X is O or S, wherein $Ar_1$ is C10 to C30 aryl, and $Ar_2$ is C6 to C30 aryl, wherein each of $R_1$ to $R_3$ is independently selected from the group consisting of halogen, C1 to C10 alkyl, C1 to C20 aryl and C3 to C10 cycloalkyl, and wherein each of a, b and c is independently an integer of 0 to 4.

14. The organic light emitting device according to claim 13, wherein the first host is selected from Formula 2:

[Formula 2]

HH-1

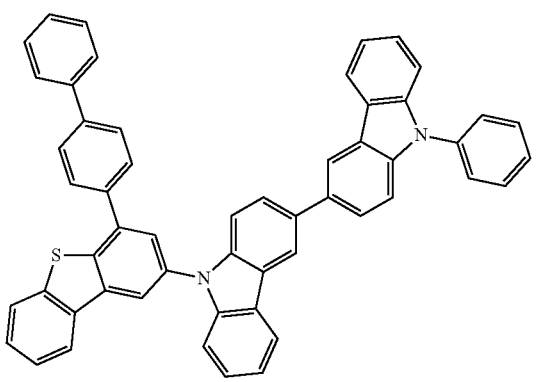

HH-2
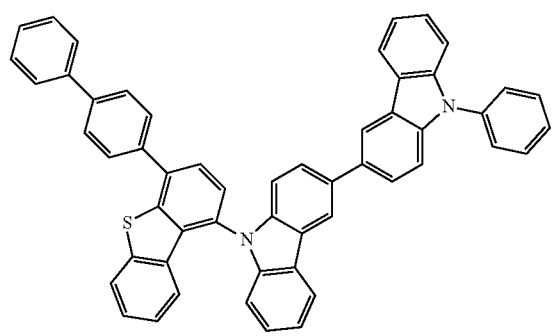
HH-3
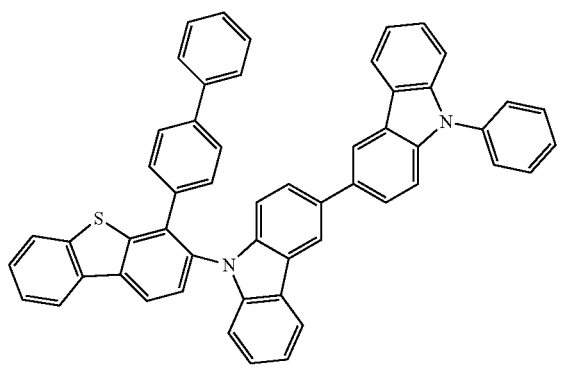
HH-4
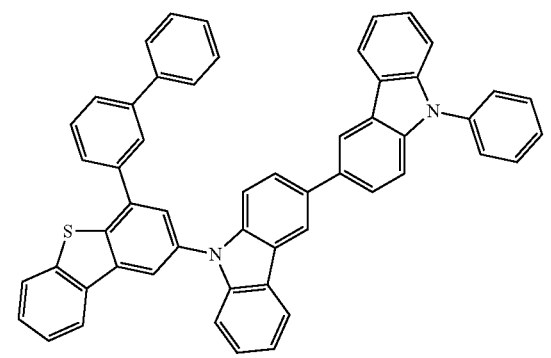
HH-5
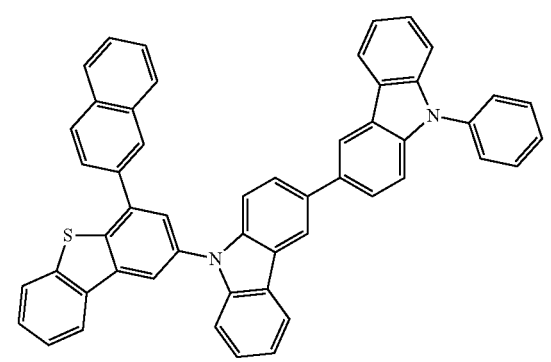
HH-6
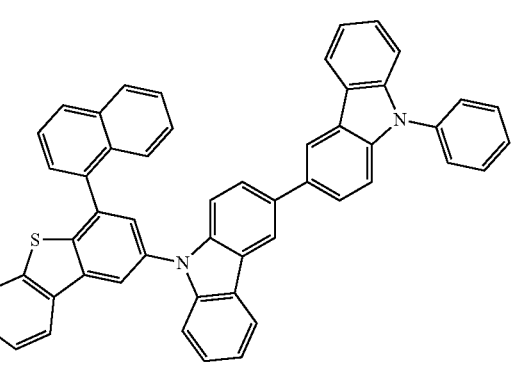
HH-7
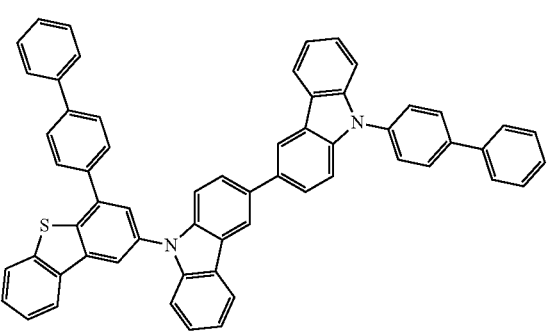
HH-8
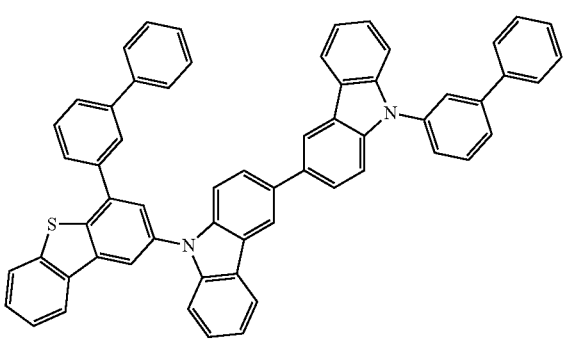
HH-9
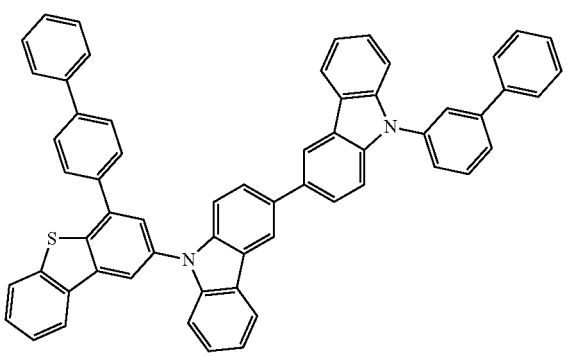

HH-10
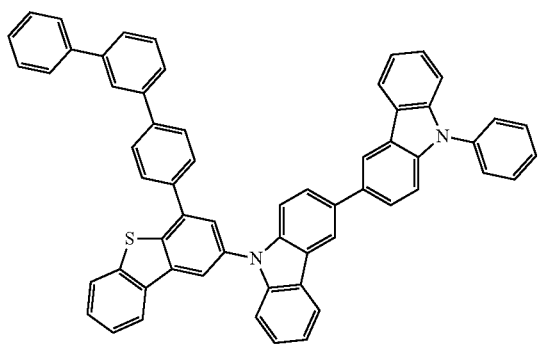
HH-11
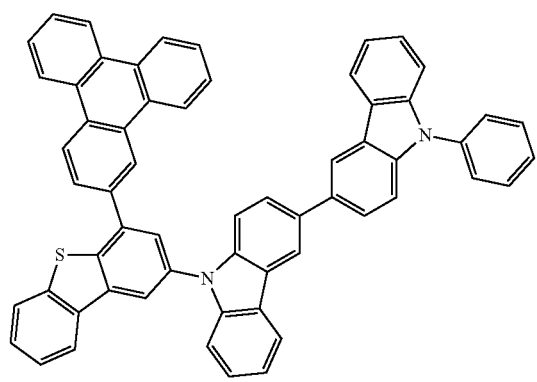
HH-12
HH-13
HH-14
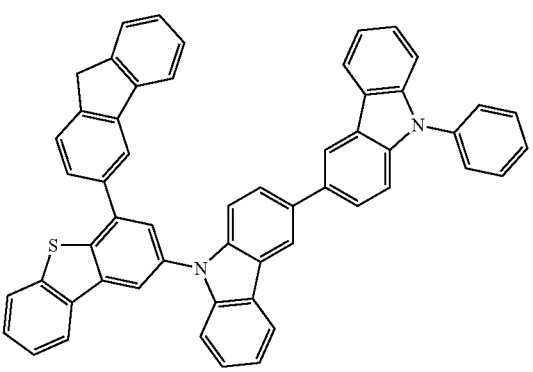
HH-15
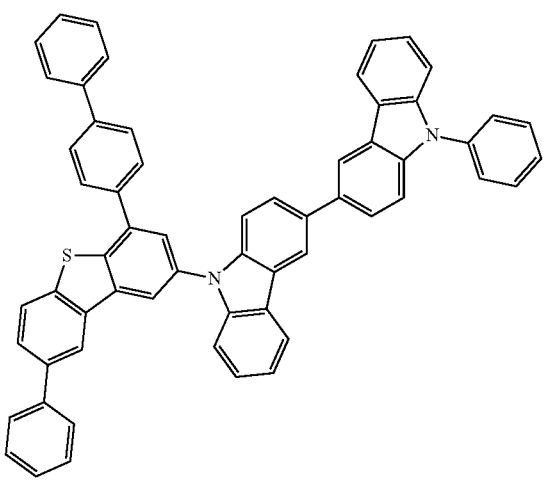
HH-16
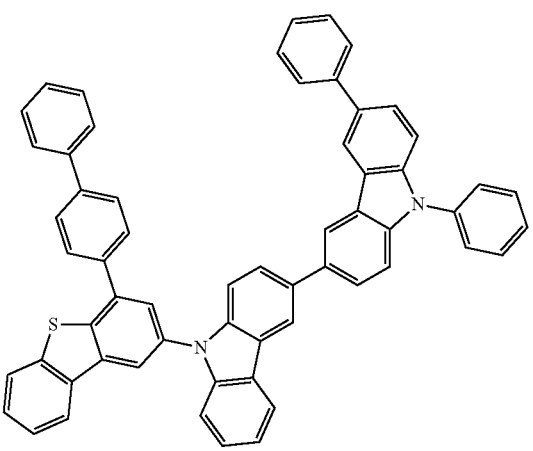

HH-17
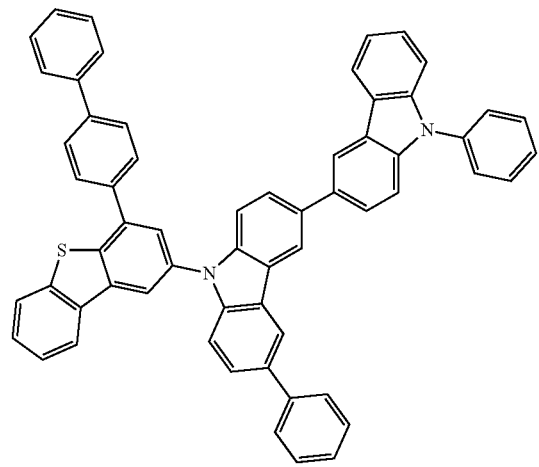
HH-18
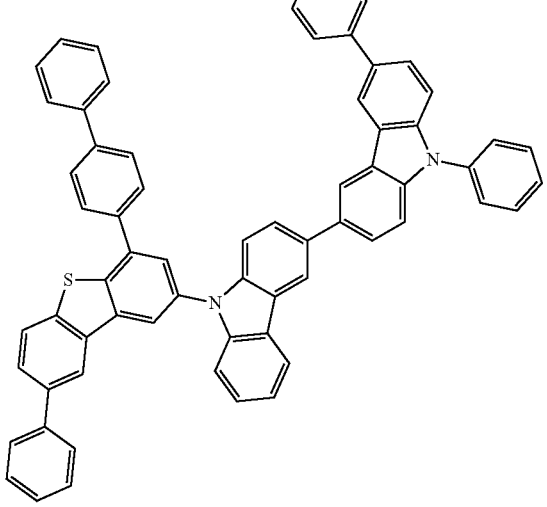
HH-19
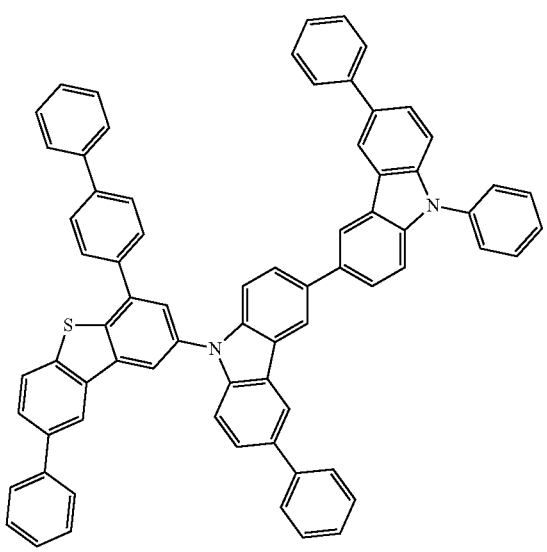
HH-20
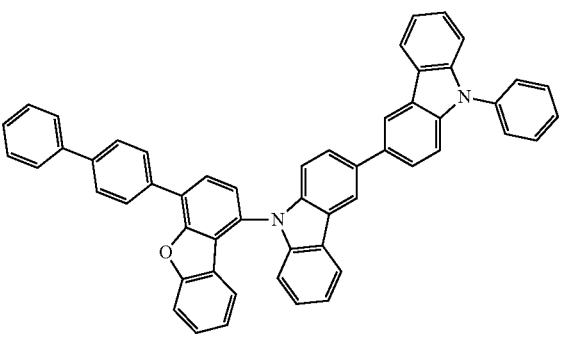
HH-21
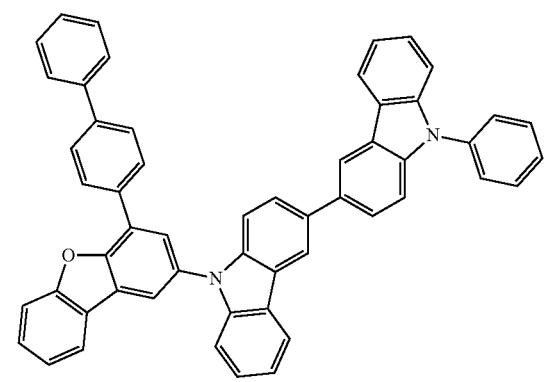
HH-22
HH-23
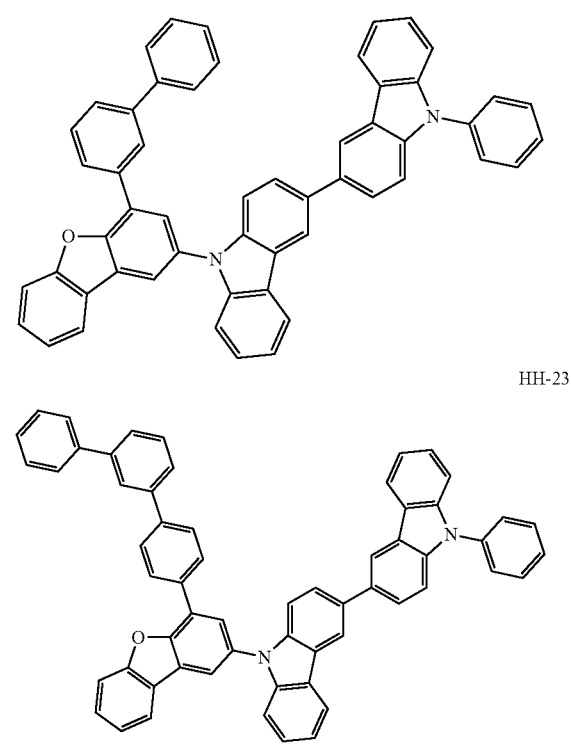

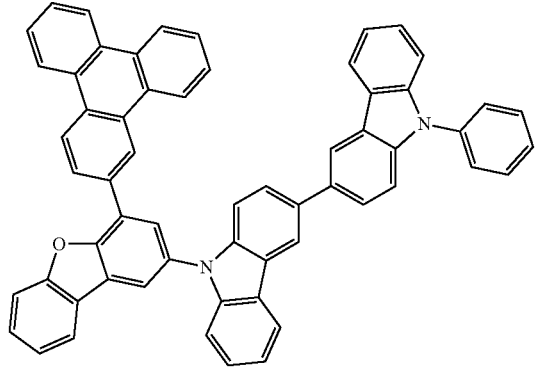
HH-24
HH-25
HH-26
HH-27
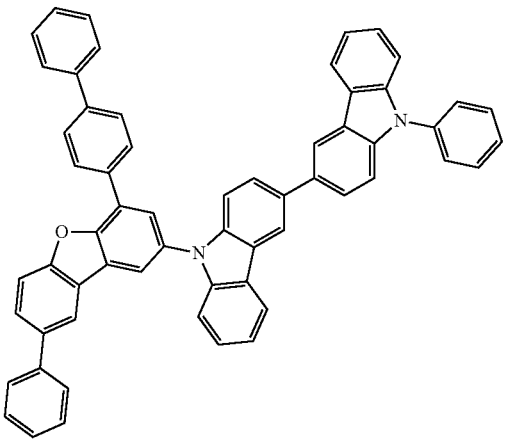
HH-28
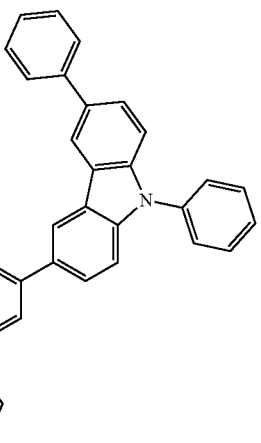
HH-29
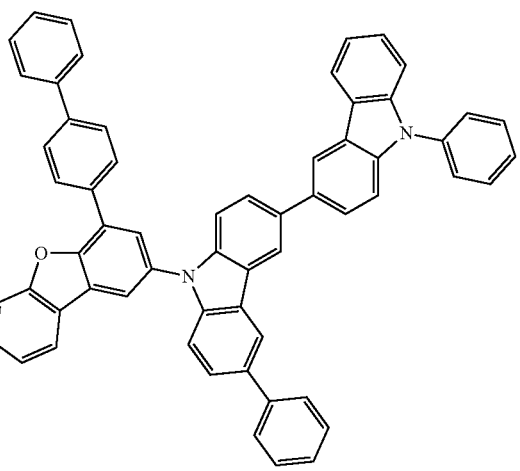
HH-30

-continued

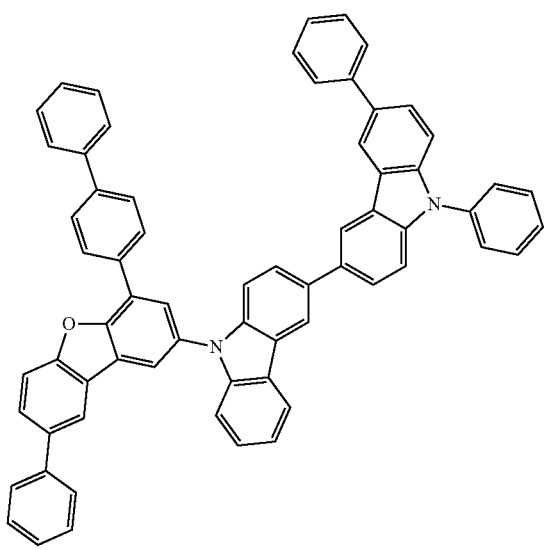
HH-31

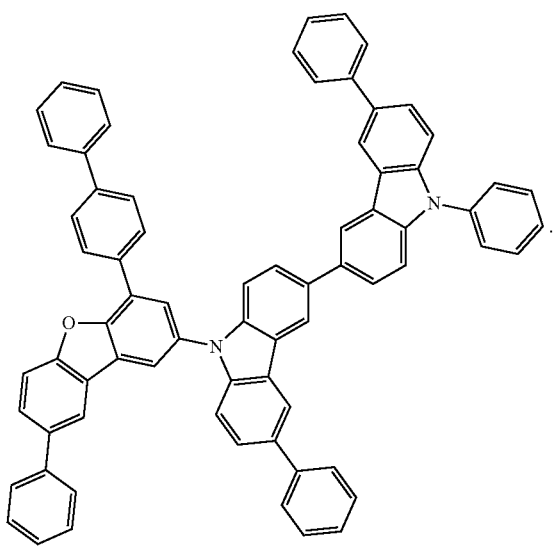
HH-32

15. The organic light emitting device according to claim 13, wherein the second host is represented by Formula 3-1:

[Formula 3-1]

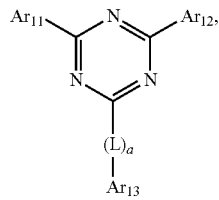

wherein each of $Ar_{11}$ and $Ar_{12}$ is independently selected from the group consisting of hydrogen and C6 to C30 aryl, wherein L is C6 to C30 arylene group, and a is 0 or 1, wherein $Ar_{13}$ may be represented by Formula 3-2 or Formula 3-3:

[Formula 3-2]

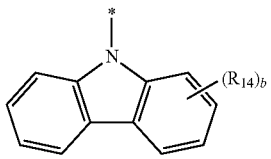

[Formula 3-3]

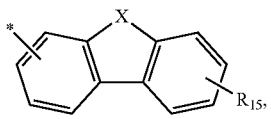

wherein in Formula 3-2, $R_{14}$ is a heteroaryl, or adjacent two $R_{14}$ form a fused ring, wherein b is an integer of 0 to 4, and wherein in Formula 3-3, $R_{15}$ is a heteroaryl, and X is O or S.

16. The organic light emitting device according to claim 15, wherein the second host is selected from Formula 4:

[Formula 4]

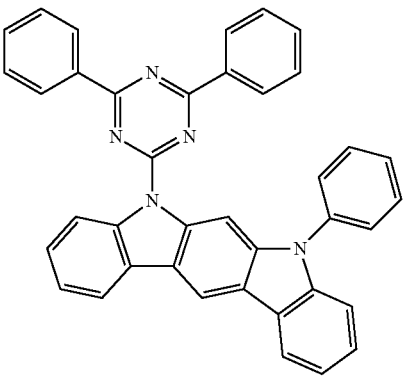
EH-1

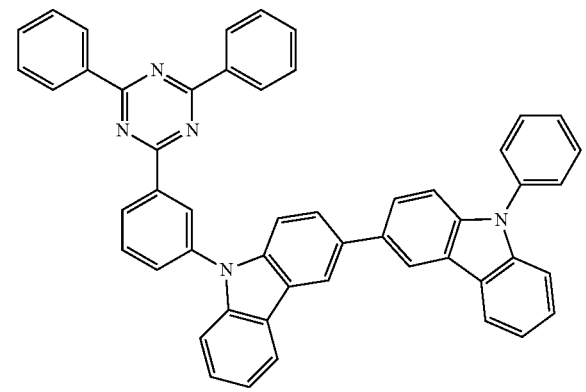
EH-2

-continued

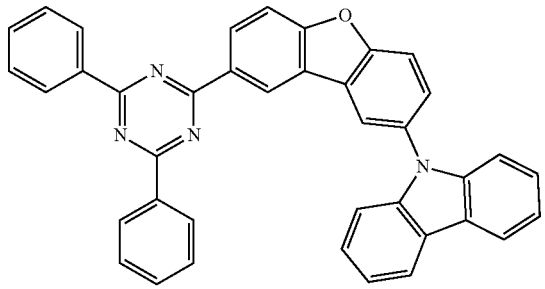
EH-3

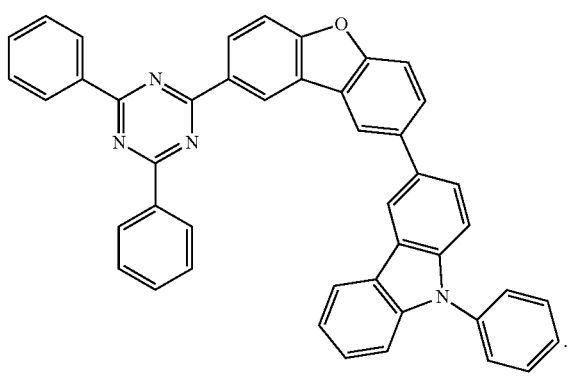
EH-4

17. The organic light emitting device according to claim 15, wherein an energy level of a triplet state of the second host is equal to or lower than an energy level of a triplet state of the first host.

18. The organic light emitting device according to claim 15, wherein a percentage by weight of the first host is equal to or greater than a percentage by weight of the second host.

19. The organic light emitting device according to claim 13, wherein the organic light emitting diode further comprises:
a hole transporting layer disposed between the first electrode and the first emitting material layer and including a hole transporting material of Formula 6:

[Formula 6]

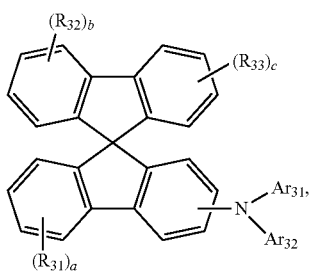

wherein each of $R_{31}$ to $R_{33}$ is independently selected from the group consisting of deuterium, halogen, C1 to C10 alkyl, C3 to C10 cycloalkyl, C6 to C30 aryl, C5 to C30 heteroaryl, trialkylsilyl and triarylsilyl, and each of $Ar_{31}$ and $Ar_{32}$ is independently selected from the group consisting of C6 to C30 aryl and C5 to C30 heteroaryl, and
wherein each of a, b and c is independently an integer of 0 to 4.

20. The organic light emitting device according to claim 19, wherein the hole transporting material is selected from Formula 7:

[Formula 7]

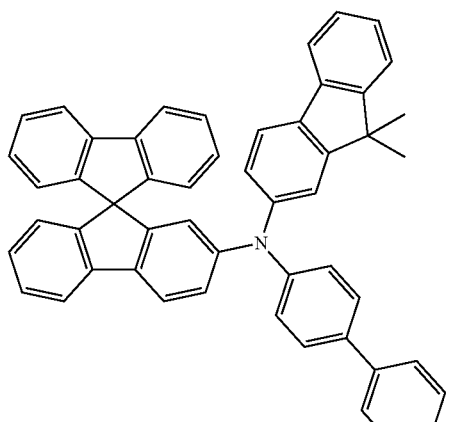
HTL-1

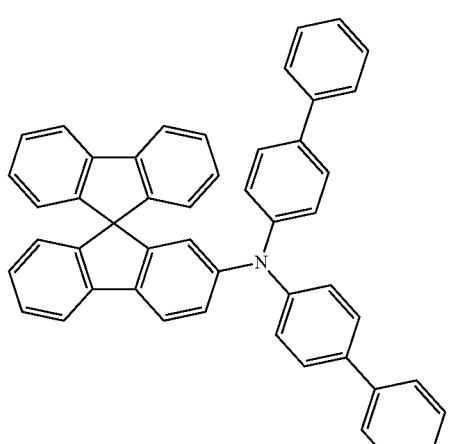
HTL-2

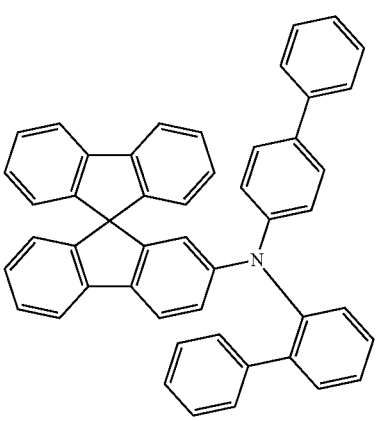
HTL-3

HTL-4
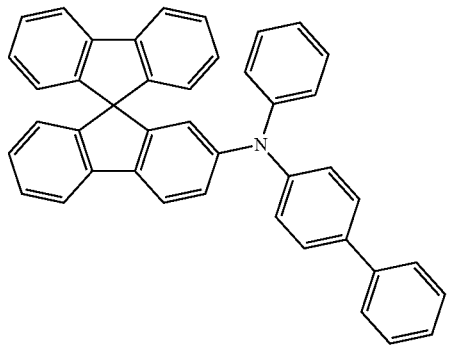
HTL-5
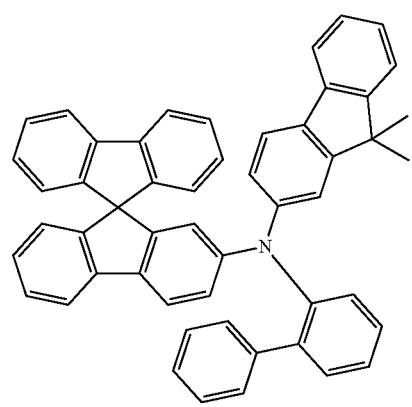
HTL-6
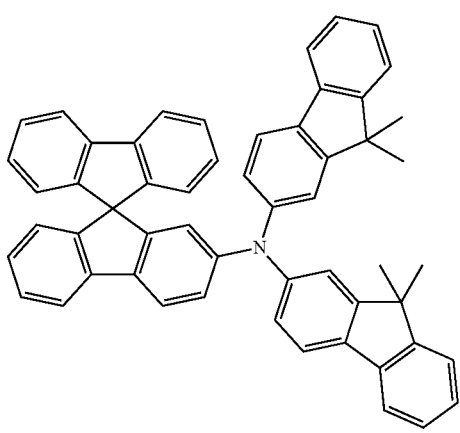
HTL-7
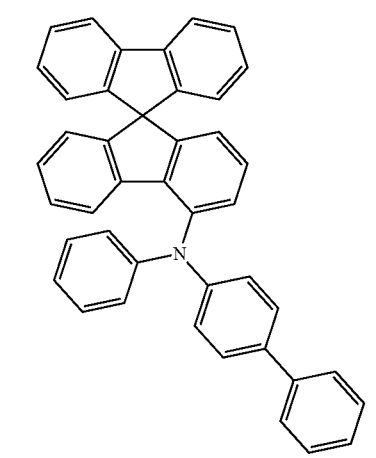
HTL-8
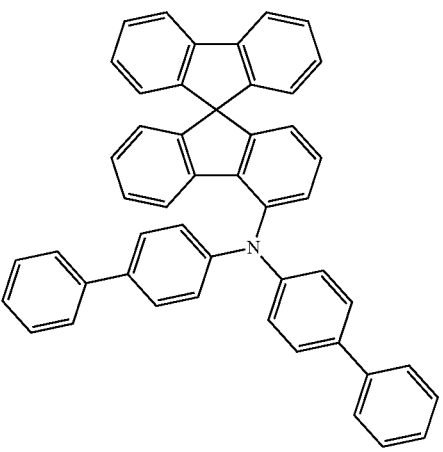
HTL-9
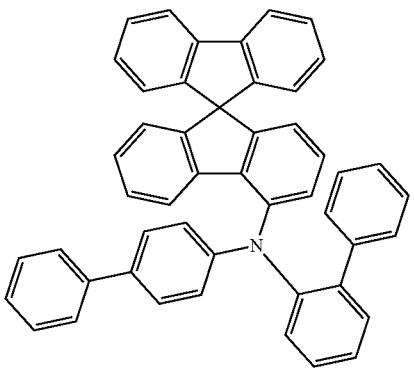
HTL-10
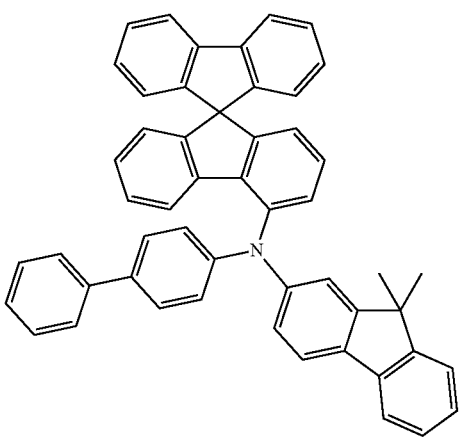

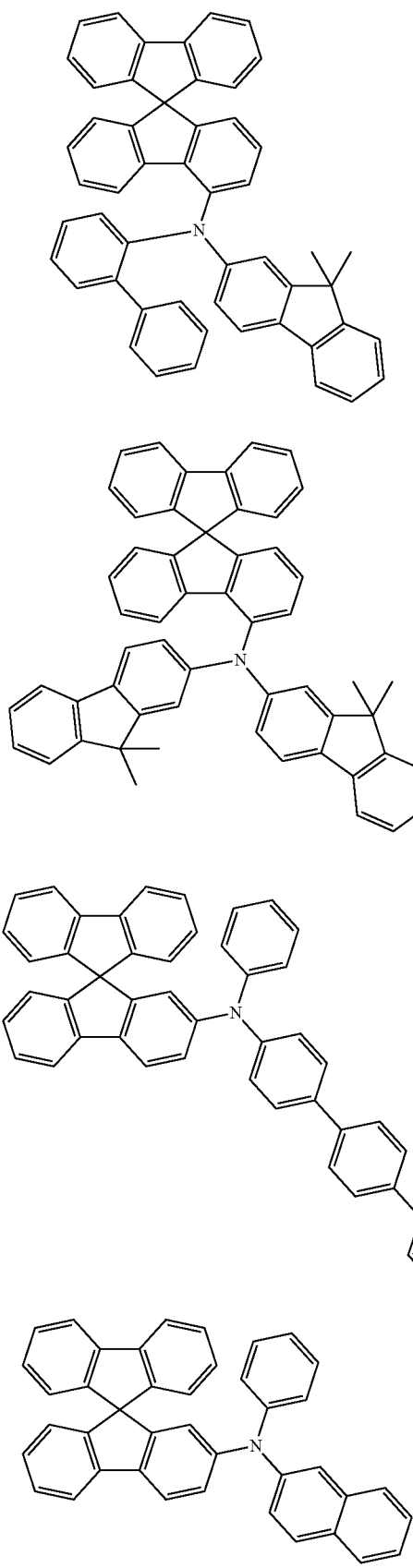
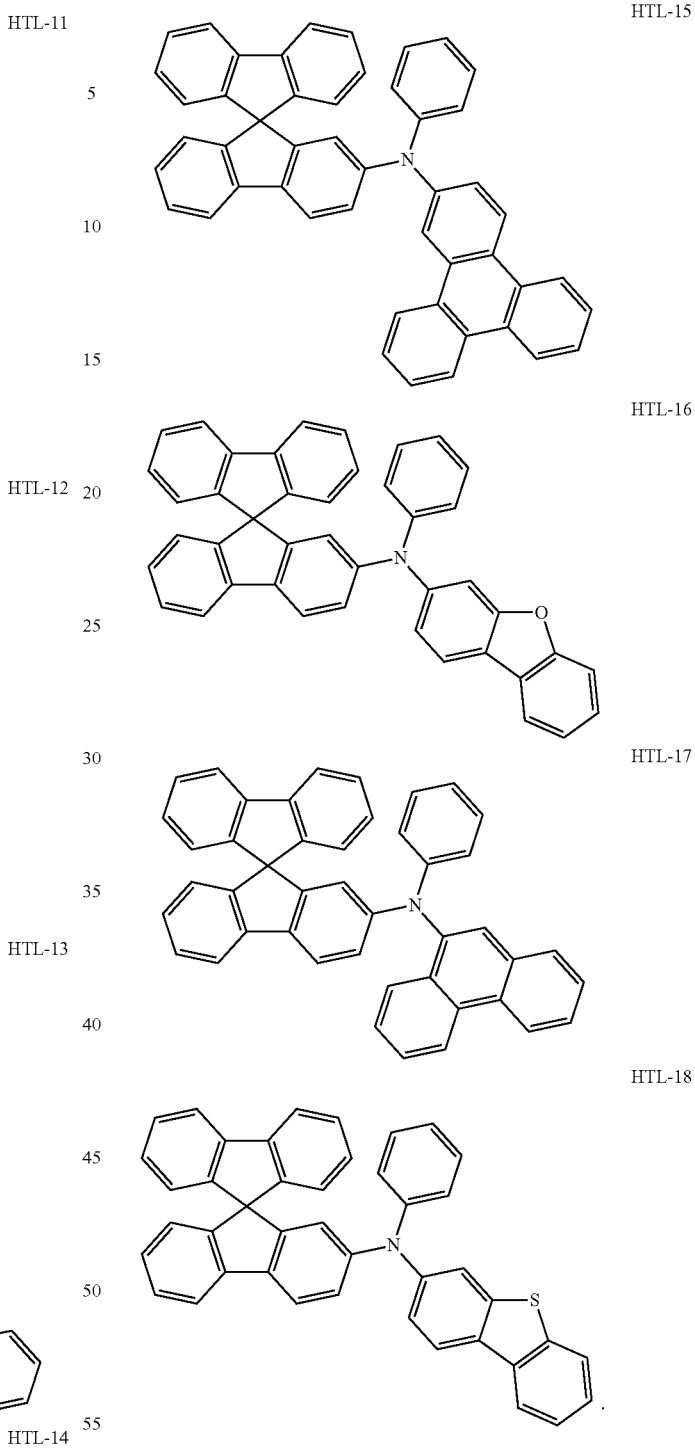

21. The organic light emitting device according to claim 19, wherein the first host has an energy level of a triplet state of 2.6 to 2.8 eV, and the second host has an energy level of a triplet state of 2.4 to 2.8 eV, and
wherein the hole transporting material has an energy level of a triplet state of 2.4 to 3.0 eV.

22. The organic light emitting device according to claim 13, wherein the first dopant is a green dopant.

23. The organic light emitting device according to claim 22, wherein the organic light emitting diode further comprises:

a second emitting material layer including a third host and a blue dopant and disposed between the first emitting material layer and the second electrode;

a charge generation layer disposed between the first and second emitting material layers; and a third emitting material layer including a fourth host and a red dopant, the third emitting material layer disposed between the first electrode and the first emitting material layer or between the first emitting material layer and the charge generation layer.

24. The organic light emitting device according to claim 23, wherein the first and third emitting material layers contact each other.

25. The organic light emitting device according to claim 23, wherein a red pixel, a green pixel and a blue pixel are defined on the substrate, and the organic light emitting diode corresponds to each of the red, green and blue pixels, and wherein the organic light emitting device further comprises:

a color filter layer corresponding to each of the red, green and blue pixels, the color filter layer disposed between the substrate and the organic light emitting diode or over the organic light emitting diode.

* * * * *